United States Patent
Pan et al.

(10) Patent No.: US 11,771,749 B2
(45) Date of Patent: Oct. 3, 2023

(54) KRAS PEPTIDE VACCINE COMPOSITIONS AND METHOD OF USE

(71) Applicant: THE MEDICAL COLLEGE OF WISCONSIN, INC., Milwaukee, WI (US)

(72) Inventors: Jing Pan, New Berlin, WI (US); Ming You, Elm Grove, WI (US); Ronald Lubet, Rockville, MD (US)

(73) Assignees: The Medical College of Wisconsin, Inc., Milwaukee, WI (US); National Institutes of Health (NIH), Bethesda, MD (US)

( * ) Notice: Subject to any disclaimer, the term of this patent is extended or adjusted under 35 U.S.C. 154(b) by 651 days.

(21) Appl. No.: 16/483,332

(22) PCT Filed: Feb. 5, 2018

(86) PCT No.: PCT/US2018/016890
§ 371 (c)(1),
(2) Date: Aug. 2, 2019

(87) PCT Pub. No.: WO2018/145020
PCT Pub. Date: Sep. 8, 2018

(65) Prior Publication Data
US 2021/0213120 A1    Jul. 15, 2021

Related U.S. Application Data

(60) Provisional application No. 62/454,270, filed on Feb. 3, 2017.

(51) Int. Cl.
| | | |
|---|---|---|
| A61K 39/00 | (2006.01) |
| A61P 35/00 | (2006.01) |
| A61K 31/192 | (2006.01) |
| A61K 31/203 | (2006.01) |
| A61K 45/06 | (2006.01) |
| A61K 31/255 | (2006.01) |

(52) U.S. Cl.
CPC .... *A61K 39/001164* (2018.08); *A61K 31/192* (2013.01); *A61K 31/203* (2013.01); *A61K 31/255* (2013.01); *A61K 45/06* (2013.01); *A61P 35/00* (2018.01); *A61K 2039/55505* (2013.01); *A61K 2039/55522* (2013.01); *A61K 2039/55572* (2013.01); *A61K 2039/86* (2018.08)

(58) Field of Classification Search
CPC .......... A61K 39/001164; A61K 31/192; A61K 31/203; A61K 31/255; A61K 45/06; A61K 2039/55505; A61K 2039/55522; A61K 2039/55572; A61K 2039/86; A61K 31/202; A61K 38/177; A61K 2039/55566; A61K 2039/572; A61K 2039/575; A61K 2039/82; A61K 2039/852; A61K 39/0011; A61P 35/00; C07K 14/4702; C07K 14/82
See application file for complete search history.

(56) References Cited

U.S. PATENT DOCUMENTS

| | | |
|---|---|---|
| 5,961,978 A | 10/1999 | Gaudernack |
| 7,030,211 B1 | 4/2006 | Gaudernack |
| 7,709,002 B1 | 5/2010 | Schlom |
| 8,852,604 B2 | 10/2014 | Kammer |
| 8,895,017 B2 | 11/2014 | Cho |
| 2006/0234339 A1 | 10/2006 | Yokoyama |
| 2007/0224208 A1* | 9/2007 | Guo ........................ A61P 35/00 435/254.2 |
| 2010/0215678 A1 | 8/2010 | Guo |
| 2014/0010831 A1 | 1/2014 | Kaumaya |
| 2014/0220059 A1 | 8/2014 | Asari |
| 2014/0234351 A1* | 8/2014 | Bender .......... A61K 39/001168 435/325 |
| 2014/0315314 A1 | 10/2014 | Dubensky, Jr. |
| 2016/0280738 A1 | 9/2016 | Mahr |

FOREIGN PATENT DOCUMENTS

| | | | |
|---|---|---|---|
| CA | 2372187 A1 | 4/2000 | |
| CN | 101448848 A | 6/2009 | |
| EP | 1862544 A1 | 12/2007 | |
| EP | 2361978 A1 | 8/2011 | |
| WO | 1992014756 A1 | 9/1992 | |
| WO | 2000066153 A1 | 11/2000 | |
| WO | 2007118660 A2 | 10/2007 | |
| WO | WO-2010037395 A2 * | 4/2010 | ......... A61K 39/0011 |
| WO | 2010037395 A2 | 8/2010 | |
| WO | 2013135266 A1 | 9/2013 | |
| WO | 2014022835 A2 | 2/2014 | |
| WO | 2014127296 A1 | 8/2014 | |
| WO | 2015169804 A1 | 11/2015 | |
| WO | 2016011386 A1 | 1/2016 | |

(Continued)

OTHER PUBLICATIONS

Ochoa R, Laio A, Cossio P. Predicting the Affinity of Peptides to Major Histocompatibility Complex Class II by Scoring Molecular Dynamics Simulations. J Chem Inf Model. Aug. 26, 2019;59(8):3464-3473 (Year: 2019).*
Dimitrov I et al. MHC Class II Binding Prediction—A Little Help from a Friend J Biomed Biotechnol. 2010; 2010: 705821 1-8 (Year: 2010).*
Jensen KK et al. Improved methods for predicting peptide binding affinity to MHC class II molecules. Immunology, 154, 394-406 (Year: 2017).*
Abrams SI, et al. Identification of overlapping epitopes in mutant ras oncogene peptides that activate CD4+ and CD8+ T cell responses. Eur J Immunol. 1996; 26(2):435-443.

(Continued)

*Primary Examiner* — Adam Weidner
*Assistant Examiner* — John J Skoko, III
(74) *Attorney, Agent, or Firm* — Quarles & Brady LLP

(57) ABSTRACT

The present disclosure provides compositions and methods of eliciting an anti-tumor immune response and treating cancer comprising at least one peptide of KRAS.

22 Claims, 15 Drawing Sheets

Specification includes a Sequence Listing.

(56) References Cited

FOREIGN PATENT DOCUMENTS

| WO | 2016156202 | A1 | 10/2016 | | |
|---|---|---|---|---|---|
| WO | 2016187508 | A2 | 11/2016 | | |
| WO | 2016202937 | A1 | 12/2016 | | |
| WO | WO-2016202937 | A1 | * | 12/2016 | ............. A61K 35/17 |

OTHER PUBLICATIONS

Bristol JA, et al. Development of a murine mutant Ras CD8+ CTL peptide epitope variant that possesses enhanced MHC class I binding and immunogenic properties. J Immunol. 1998; 160(5):2433-2441.

Carbone DP, et al. Immunization with mutant p53- and K-ras-derived peptides in cancer patients: immune response and clinical outcome. J Clin Oncol. 2005; 23(22):5099-5107.

Cox AD, et al. Drugging the undruggable RAS: Mission possible? Nat Rev Drug Discov. 2014; 13(11):828-851.

Disis ML, et al. A multiantigen vaccine targeting neu, IGFBP-2, and IGF-IR prevents tumor progression in mice with preinvasive breast disease. Cancer Prev Res (Phila). 2013; 6(12):1273-1282.

Ebben JD, et al. Epidermal growth factor receptor derived peptide vaccination to prevent lung adenocarcinoma formation: An in vivo study in a murine model of EGFR mutant lung cancer. Mol Carcinog. 2015.

Garzón, M., et al. "KRAS mutations in the circulating free DNA (cfDNA) of non-small cell lung cancer (NSCLC) patients." Translational lung cancer research 5.5 (2016): 511.

Gjertsen MK, et al. Cytotoxic CD4+ and CD8+ T lymphocytes, generated by mutant p21-ras (12Val) peptide vaccination of a patient, recognize 12Val-dependent nested epitopes present within the vaccine peptide and kill autologous tumour cells carrying this mutation. Int J Cancer. 1997; 72(5):784-790.

Gjertsen MK, et al. Ex vivo ras peptide vaccination in patients with advanced pancreatic cancer: results of a phase I/II study. Int J Cancer. 1996; 65(4):450-453.

Gjertsen MK, et al. Intradermal ras peptide vaccination with granulocyte-macrophage colony-stimulating factor as adjuvant: Clinical and immunological responses in patients with pancreatic adenocarcinoma. Int J Cancer. 2001; 92(3):441-450.

Gjertsen, M., et al. "HLA-A3 restricted mutant ras specific cytotoxic T-lymphocytes induced by vaccination with T-helper epitopes." Journal of molecular medicine 81.1 (2003): 43-50.

Hanson HL, et al. CD4-directed peptide vaccination augments an antitumor response, but efficacy is limited by the number of CD8+ T cell precursors. J Immunol. 2004; 172(7):4215-4224.

Hartmaier, R. J., et al. "Genomic analysis of 63,220 tumors reveals insights into tumor uniqueness and targeted cancer immunotherapy strategies." Genome medicine 9.1 (2017): 16.

International Searching Authority, International Search Report and Written Opinion for application PCT/US2018/016890, dated Apr. 27, 2018, 17 pages.

Khleif SN, et al. A phase I vaccine trial with peptides reflecting ras oncogene mutations of solid tumors. J Immunother. 1999; 22(2):155-165.

Meyer RG, et al. An open-label, prospective phase I/II study evaluating the immunogenicity and safety of a ras peptide vaccine plus GM-CSF in patients with non-small cell lung cancer. Lung Cancer. 2007; 58(1):88-94.

Mittendorf EA, et al. Vaccination with a HER2/neu peptide induces intra- and inter-antigenic epitope spreading in patients with early stage breast cancer. Surgery. 2006; 139(3):407-418.

Nicklas, W. 1992; Aluminum salts. Research in Immunology 143(5):489-493.

Ostrem JM et al. Direct small-molecule inhibitors of KRAS: from structural insights to mechanism-based design. Nat Rev Drug Discov. 2016; 15(11):771-785.

Park KH, et al. Insulin-like growth factor-binding protein-2 is a target for the immunomodulation of breast cancer. Cancer Res. 2008; 68(20):8400-8409.

Prior IA, et al. A comprehensive survey of Ras mutations in cancer. Cancer Res. 2012; 72(10):2457-2467.

Roy DM, et al. Driver mutations of cancer epigenomes. Protein Cell. 2014; 5(4):265-296.

Selene et al. "Cyclooxygenase-Dependent Tumor Growth through Evasion of Immunity" 2015, Cell 162, 1257-1270.

Shaabani, S., et al. "A patent review on PD-1/PD-L1 antagonists: small molecules, peptides, and macrocycles (2015-2018)." Expert opinion on therapeutic patents 28.9 (2018): 665-678.

Shames DS et al. The evolving genomic classification of lung cancer. J Pathol. 2014; 232(2):121-133.

Shono, Y., et al. "Specific T-cell immunity against Ki-ras peptides in patients with pancreatic and colorectal cancers." British journal of cancer 88.4 (2003): 530.

Torre LA, et al. Global cancer statistics, 2012. CA Cancer J Clin. 2015; 65(2):87-108.

Toubaji A, et al. Pilot study of mutant ras peptide-based vaccine as an adjuvant treatment in pancreatic and colorectal cancers. Cancer Immunol Immunother. 2008; 57(9):1413-1420.

Vogelstein B, et al. Cancer genome landscapes. Science. 2013; 339(6127):1546-1558.

Zelenay, S., et al. "Cyclooxygenase-dependent tumor growth through evasion of immunity." Cell 162.6 (2015):1257-1270.

CN 201880023091.7—First Office Action, dated Nov. 25, 2022.

Toubaji, et al., "Pilot study of mutant ras peptide-based vaccine as an adjuvant treatment in pancreatic and colorectal cancers" Cancer Immunology, Immunotherapy vol. 57, pp. 1413-1420 (2008).

Rahma, et al., "The immunological and clinical effects of mutated ras peptide vaccine in combination with IL-2, GM-CSF, or both in patients with solid tumors" Journal of Translational Medicine vol. 12, Article No. 55 (2014).

* cited by examiner

FIGS. 4A-4E
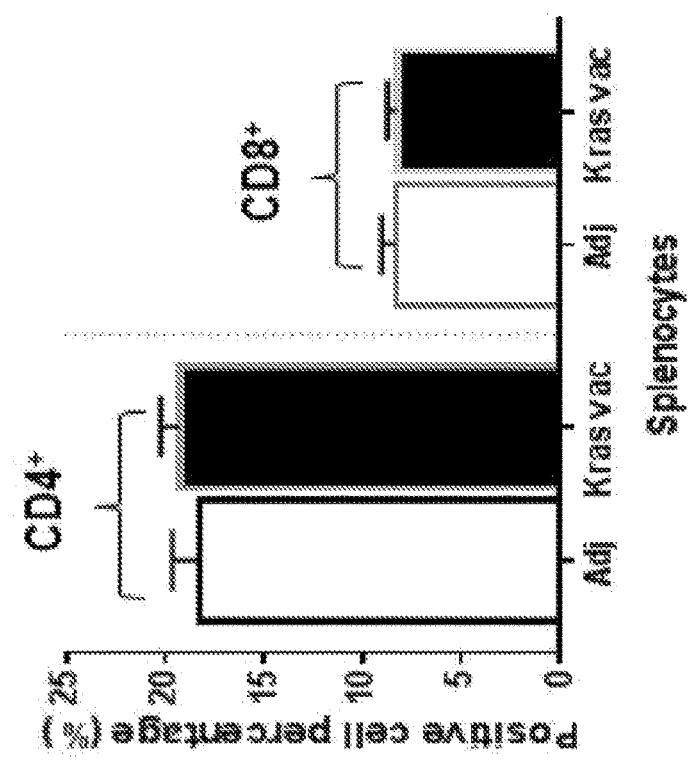
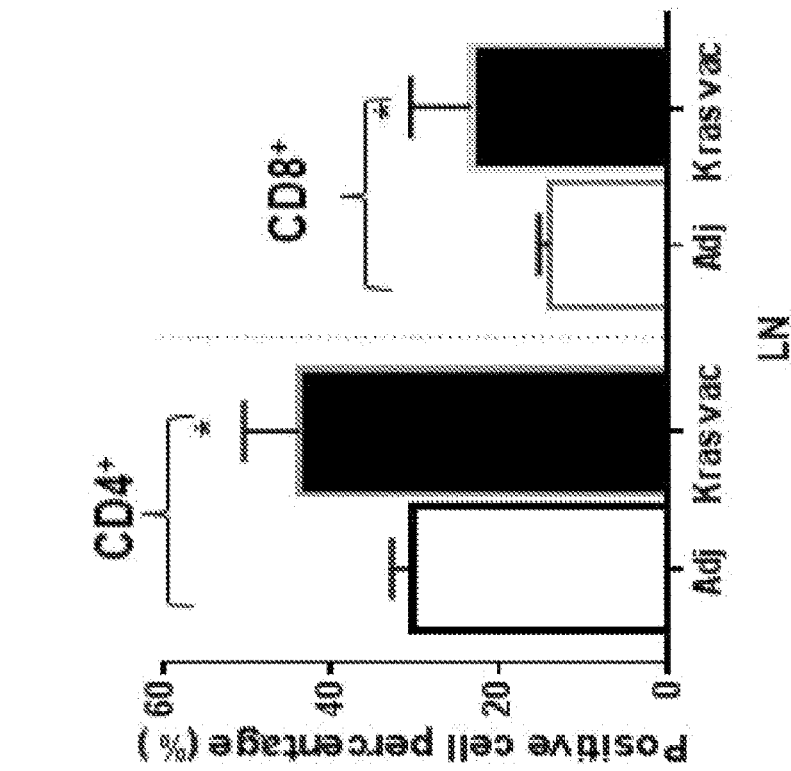

Days post tumor cell inoculation

KRAS PEPTIDE VACCINE COMPOSITIONS AND METHOD OF USE

CROSS-REFERENCE TO RELATED APPLICATIONS

This application is a U.S. national stage application of PCT Application No. PCT/US18/016890 filed on Feb. 5, 2018, which claims priority to U.S. Provisional Application No. 62/454,270 filed on Feb. 3, 2017, the contents of which are incorporated by reference in their entireties.

REFERENCE TO A SEQUENCE LISTING SUBMITTED VIA EFS-WEB

A Sequence Listing accompanies this application and is submitted as an ASCII text file of the sequence listing named "650053_00627_ST25.txt" which is 14 KB in size and was created on Feb. 8, 2021. The sequence listing is electronically submitted via EFS-Web with the application and is incorporated herein by reference in its entirety.

STATEMENT REGARDING FEDERALLY SPONSORED RESEARCH

N/A

BACKGROUND OF THE INVENTION

The field of the invention is vaccine for treatment and prevention of cancer. More particularly, the invention relates to KRAS peptides.

Lung cancer, which has a low five-year survival rate, remains the leading cause of cancer death worldwide, with cases rising globally [1]. New approaches are needed to improve the clinical outcome for these patients. A number of genetic and epigenetic abnormalities are identified as essential drivers promoting tumor development [2, 3]. This has facilitated the identification and characterization of potential tumor antigens that have become relevant targets for the development of cancer vaccines. Among the oncogenes in NSCLC (non-small cell lung cancer), mutations of the Kirsten rat sarcoma viral oncogene homolog (KRAS) are most frequently observed. They may represent up to 30% of lung cancer in the Caucasian smoking population [4], with 80% of them are specifically altered in codon 12 [5]. No specific targeted therapies have been developed, partially due to the lack of druggable pockets and cavities on the RAS surface [6], except for the new compounds recently discovered that specifically target mutant $KRAS^{G12C}$ [7], the development of alternative therapies or preventive measures has great appeal.

Peptide vaccination against tumor-associated antigen as a means of treating cancer patients or preventing the development of tumors in high-risk individuals (e.g., former or current smokers) is currently an area of intense research [8]. Peptide vaccines can elicit memory T cells that remain in lymph nodes until exposed to the target antigen. After stimulation, T cells migrate to the site of antigen-expressing lesions regardless of the location and will proliferate and destroy those lesions. Numerous investigators have attempted to inhibit mutant KRAS, often employing relatively short MHC class I restricted peptides with minimal to moderate success [9, 10]. We, however, have taken a rather different approach by employing longer peptides with predicted binding affinity to MHC class II. Using this approach, we and our collaborators have previously developed a multipeptide multivalent vaccine that elicited robust Th1 immune responses and effectively blocked the development of neu-driven mammary tumors [11], or mutant EGFR1-driven lung cancer [12]. These studies show that one can generate effective MHC class II-mediated immune responses against a variety of target peptides despite potential tolerance. The latter study also highlights that one can induce effective immunity against an overexpressed mutant protein without directly immunizing with the mutant peptide itself.

Thus, there is a need for compositions and methods of eliciting an effective anti-tumor immune response in numerous cancers.

SUMMARY OF THE INVENTION

The disclosure provides vaccine compositions and methods for treatment of cancer, including lung, pancreatic and colon cancer, as described in the specification and claims herein.

The present invention demonstrates both the immunogenicity and antitumor efficacy of newly formulated multipeptide (peptides 15-17 amino acids long) vaccine targeting multiple epitopes of the KRAS molecule in a mouse model of a KRAS-driven lung tumor. A multipeptide KRAS vaccine was immunogenic and efficacious in the primary prevention of KRAS-induced lung cancer, indicating that the approach can be used to prevent other KRAS-driven cancers, either alone or in combination with other modalities.

The present invention provides MHC class II peptides of KRAS that are able to elicit an anti-tumor immune response in a subject. In some aspect, a combination of MHC class II peptides that elicit a robust and anti-tumor immune response in a subject. In some aspects, the present invention provides a combination of at least one MHC class II peptide of KRAS in combination with at least one MHC class I peptide of KRAS to provide an anti-tumor response. The MHC class I or class II peptides are able to target epitopes that lead to a robust and anti-tumor immune response.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A-4F. Immunologic Consequences of Vaccination. (A) KRAS vaccine promotes CD4+/CD8 cells in lymph nodes. Representative flow cytometry results for CD4/CD8 cells from mediastinal lung draining lymph nodes (A, upper panels) and spleen (A, lower panels). (B, C) CD8+ cells expressed as a percentage of total live cells isolated from the lung tumor draining lymph nodes or spleens of adjuvant treated and vaccinated animals at the experimental endpoint (right two columns in B and C); CD4+ cells expressed as a percentage of total live cells isolated from the lung tumor draining lymph nodes or spleens of adjuvant treated and vaccinated animals at the experimental endpoint (left two columns in B and C). (D) Tregs were not increased by the KRAS peptide vaccine. Representative flow cytometry data for FoxP3+ cells expressed as a percentage of the total live CD4+ pool isolated from the lungs and spleens of adjuvant treated and vaccinated animals at the experimental endpoint. (E) KRAS doesn't increase the number of CD8+ tumor infiltrating lymphocytes cells in treated animals. (F) KRAS increases the number of CD4+ tumor infiltrating lymphocytes in treated animals.

Mice were treated with the combination of K-ras multipeptide vaccine with avasimibe in a K-ras-driven lung cancer syngraft model. Tumor volume was assessed over time post tumor cell inoculation.

Figure 11:
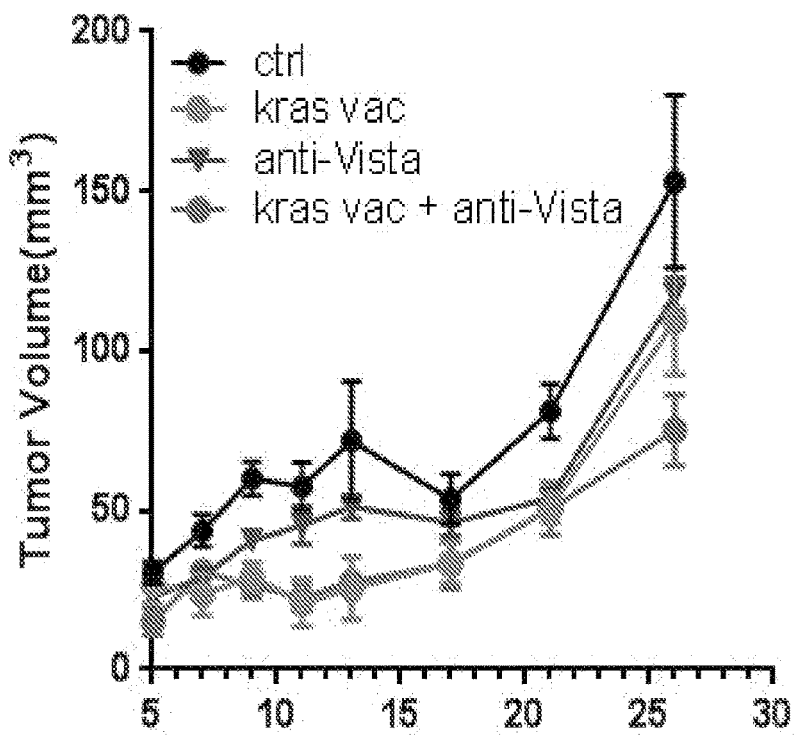

FIG. 11. K-ras vaccine synergize with immune checkpoint inhibitor anti-Vista to inhibit pancreatic cancer progression in K-ras-driven pancreatic cancer syngraft tumor model. Mice were treated with anti-VISTA combined with K-RAS vaccine in a pancreatic cancer tumor model. Tumor volume was assayed over time after administration.

Figure 12:
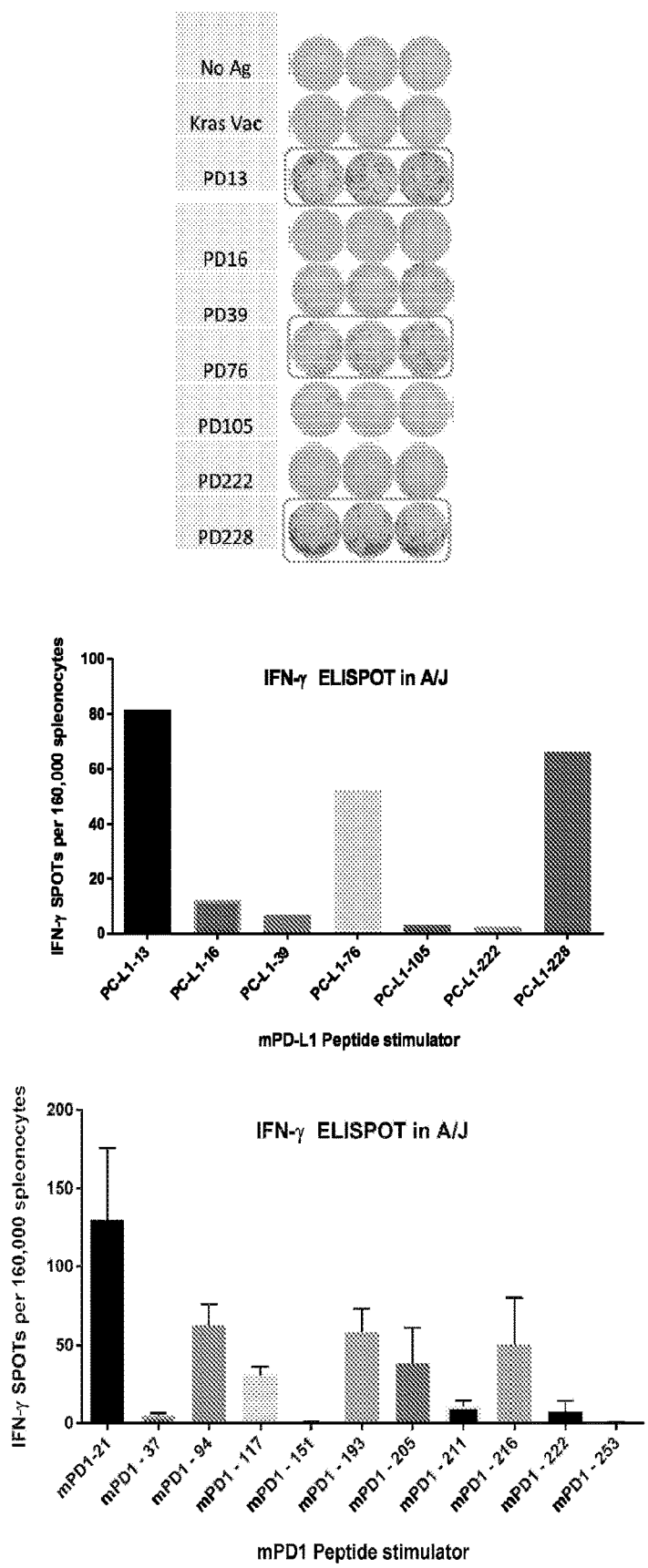

FIG. 12. Select most immunogenic peptides for PD-L1 or PD-1.

The immunogenicity of PD-1 and PD-L1 were tested in naïve mice using the IFN-γ ELISPOT assay. (P<0.0001, data not shown)

Figure 13:
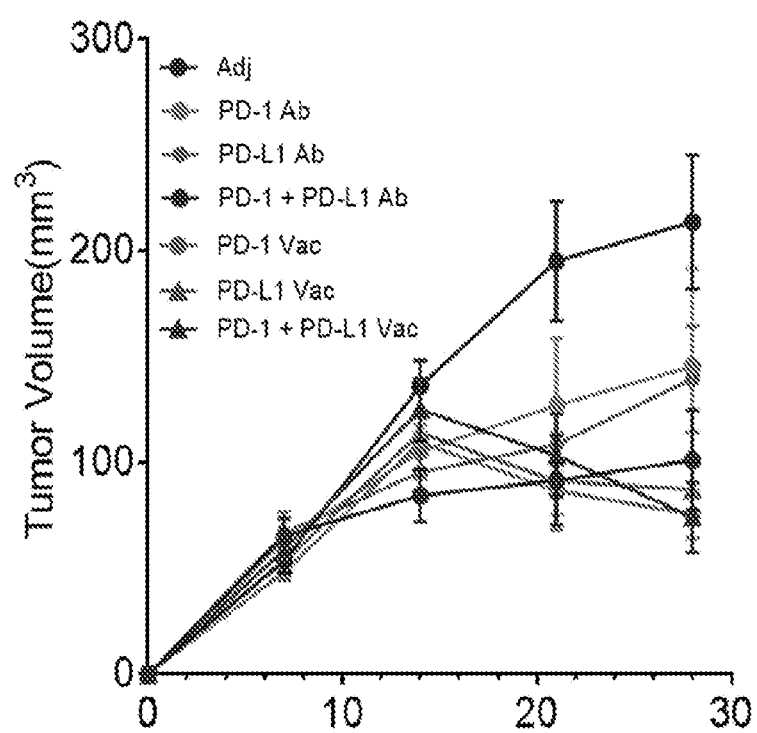

FIG. 13. PD-1/PD-L1 peptide vaccine is effectively inhibit tumor growth in a K-ras-driven lung cancer syngraft tumor model. Mice were treated with PD-1 antibody, PD-L1 antibody, a combination of PD-1 and PD-L1 antibody, or a vaccine comprising PD-1 peptide (Table 3: mPD1-21, mPD1-94, mPD1-193, and mPD1-216), PD-L1 peptide (Table 3: mPDL1-13, mPDL1-76, and mPDL1228), or a combination of PD-1 and PD-L1 peptide (Table 3: mPD1-21, mPD1-94, mPD1-193, mPD1-216 and mPDL1-13, mPDL1-76, mPDL1228) in the mouse lung cancer tumor model. The tumor volume was monitored over time.

DETAILED DESCRIPTION OF THE INVENTION

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a," "an," and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

The present invention provides peptides, nucleic acid sequences encoding the peptides, and compositions containing the peptides (and in some instances specific combinations of two or more peptides) that can be used to elicit an anti-tumor response in a subject. Further, methods of treating, preventing, or reducing the progression of cancer are also provided. Suitably, the peptides specifically elicit an MHC class II mediated T cell response, which results in the treatment, reduction or elimination of a tumor in a patient.

The term "treating" or "treatment" of cancer includes, but is not limited to, reducing, inhibiting or preventing the growth or spread of cancer cells, reducing, inhibiting or preventing metastasis of a primary tumor and/or reducing, inhibiting or preventing one or more symptoms of cancer or metastasis thereof.

The terms "tumor cell growth" or "tumor cell proliferation" are used herein interchangeably to refer to the increase in number of tumor cells.

The terms "cancer" and "tumor" are used herein interchangeably. The term cancer or tumor refer to or describe the physiological condition in mammals in which a population of cells are characterized by unregulated or abnormal cell growth that originates in an organ of the mammal. The term cancer refer to both the primary cancer and secondary (metastatic) lesions thereof.

Suitable cancers that can be treated or prevented by the methods described herein include, but are not limited to, KRAS-associated cancers, including, for example, cancers associated with a mutated KRAS gene, cancers having abnormal or upregulated expression of KRAS and the like. Specifically, suitable cancers that may be treatment by the methods described herein include, but are not limited to, lung cancer, non-small lung cancer (NSCLC), pancreatic cancer, and colon cancer.

Other cancers that may have a mutated or misregulated KRAS gene may also be treated or prevented by the methods described herein. These cancers may include, but are not limited to, for example urogenital, gynecological, lung, gastrointestinal, head and neck cancer, malignant glioblastoma, malignant mesothelioma, non-metastatic or metastatic breast cancer, malignant melanoma, Merkel Cell Carcinoma or bone and soft tissue sarcomas, haematologic neoplasias, multiple myeloma, acute myelogenous leukemia, chronic myelogenous leukemia, myelodysplastic syndrome and acute lymphoblastic leukemia, breast cancer, metastatic colorectal cancers, hormone sensitive or hormone refractory prostate cancer, colorectal cancer, ovarian cancer, hepatocellular cancer, renal cell cancer, pancreatic cancer, gastric cancer, esophageal cancers, hepatocellular cancers, cholangiocellular cancers, head and neck squamous cell cancer soft tissue sarcoma, and small cell lung cancer. In a preferred embodiment, the cancers are pancreatic cancer, lung cancer or colon cancer. Specifically, in some embodiments, the cancers are pancreatic cancer, lung cancer or colon cancer that have mutated or misregulated KRAS gene.

In one embodiment, the present invention provides isolated MHC class II associated antigenic peptides comprising an amino acid sequence from KRAS that is less than 26 amino acids in length and able to bind to and be presented by MHC class II molecules on antigen presenting cells. The MHC class II associated antigenic peptides comprise, consisting essentially of, consists of, or are an amino acid sequence selected from the group consisting of SEQ ID Nos. 1, 2, 3, 4, 5, 6, 7, 8, 9, 10, 11, and 12 as depicted in Table. 1 or an amino acid sequence having at least 70%, alternatively at least 75%, alternatively at least 80%, alternatively at least 85%, alternatively at least 90%, alternatively at least 95%, alternatively at least 98%, alternatively at least 99%, alternatively 100% sequence identity to the amino acid sequence of SEQ ID Nos. 1, 2, 3, 4, 5, 6, 7, 8, 9, 10, 11, or 12. Preferably, the antigenic polypeptides have a length of less than 26 amino acids, more preferably a length of 11 to 25 amino acids. In some embodiments, the polypeptides are about 14-18 amino acids in length, alternatively about 15 to 17 amino acids in length.

The polypeptides of the present invention are preferentially presented on MHC class II molecules on antigen presenting cells.

In some embodiments, the disclosure provides a vaccine composition comprising (1) at least one peptide of KRAS, wherein the peptide comprising an amino acid sequence selected from the group consisting of SEQ ID Nos. 4, 5, 6, 7, 8, 9, 10, 11 or 12 or an amino acid sequence having at least 70% sequence identity to the amino acid sequence of SEQ ID Nos. 4, 5, 6, 7, 8, 9, 10, 11 or 12, or (2) a vector comprising a nucleic acid sequence encoding the polypeptide sequence of any one of SEQ ID Nos. 4-12 or an amino acid sequence having at least 70% sequence identity to the amino acid of any one of SEQ ID Nos. 4-12; and an adjuvant, wherein the vaccine composition elicits an anti-tumor immune response in a subject.

In other embodiments, the disclosure provides a vaccine composition comprising at least two MHC class II peptides of KRAS, wherein the at least two peptides of KRAS are selected from an amino acid sequence of any one of SEQ ID Nos. 1, 2, 3, 4, 5, 6, 7, 8, 9, 10, 11 or 12 found in Table 1, amino acid sequences having at least 70% sequence identity to any one of SEQ ID NO. 1, 2, 3, 4, 5, 6, 7, 8, 9, 10, 11 or 12, amino acid sequences having at least 85% sequence identity to any one of SEQ ID NO. 1, 2, 3, 4, 5, 6, 7, 8, 9, 10, 11 or 12, amino acid sequences having at least 90% sequence identity to any one of SEQ ID NO. 1, 2, 3, 4, 5, 6, 7, 8, 9, 10, 11 or 12, amino acid sequences having at least 95% sequence identity to any one of SEQ ID NO. 1, 2, 3, 4, 5, 6, 7, 8, 9, 10, 11 or 12, amino acid sequences having at least 98% sequence identity to any one of SEQ ID NO. 1, 2, 3, 4, 5, 6, 7, 8, 9, 10, 11 or 12, amino acid sequence having at least 99% sequence identity to any one of SEQ ID NO. 1, 2, 3, 4, 5, 6, 7, 8, 9, 10, 11 or 12, or amino acid sequences having 100% sequence identity to the amino acid sequence of SEQ ID Nos. 1, 2, 3, 4, 5, 6, 7, 8, 9, 10, 11 or 12.

In other embodiments, the disclosure provides a vaccine composition comprising at least three MHC class II peptides of KRAS, wherein the at least three peptides of KRAS are selected from an amino acid sequence of any one of SEQ ID Nos. 1, 2, 3, 4, 5, 6, 7, 8, 9, 10, 11, or 12 found in Table 1, amino acid sequences having at least 70% sequence identity to any one of SEQ ID NO. 1, 2, 3, 4, 5, 6, 7, 8, 9, 10, 11, or 12, amino acid sequences having at least 85% sequence identity to any one of SEQ ID NO. 1, 2, 3, 4, 5, 6, 7, 8, 9, 10, 11, or 12, amino acid sequences having at least 90% sequence identity to any one of SEQ ID NO. 1, 2, 3, 4, 5, 6, 7, 8, 9, 10, 11, or 12, amino acid sequences having at least 95% sequence identity to any one of SEQ ID NO. 1, 2, 3, 4, 5, 6, 7, 8, 9, 10, 11, or 12, amino acid sequences having at least 98% sequence identity to any one of SEQ ID NO. 1, 2, 3, 4, 5, 6, 7, 8, 9, 10, 11, or 12, amino acid sequence having at least 99% sequence identity to any one of SEQ ID NO. 1, 2, 3, 4, 5, 6, 7, 8, 9, 10, 11, or 12, or amino acid sequences having 100% sequence identity to the amino acid sequence of SEQ ID Nos. 1, 2, 3, 4, 5, 6, 7, 8, 9, 10, 11, or 12.

In other embodiments, the disclosure provides a vaccine composition comprising at least four peptides of KRAS, wherein the at least four peptides of KRAS are selected from an amino acid sequence of any one of SEQ ID Nos. 1, 2, 3, 4, 5, 6, 7, 8, 9, 10, 11, or 12 found in Table 1, amino acid sequences having at least 70% sequence identity to any one of SEQ ID NO. 1, 2, 3, 4, 5, 6, 7, 8, 9, 10, 11, or 12, amino acid sequences having at least 85% sequence identity to any one of SEQ ID NO. 1, 2, 3, 4, 5, 6, 7, 8, 9, 10, 11, or 12, amino acid sequences having at least 90% sequence identity to any one of SEQ ID NO. 1, 2, 3, 4, 5, 6, 7, 8, 9, 10, 11, or 12, amino acid sequences having at least 95% sequence identity to any one of SEQ ID NO. 1, 2, 3, 4, 5, 6, 7, 8, 9, 10, 11, or 12, amino acid sequences having at least 98% sequence identity to any one of SEQ ID NO. 1, 2, 3, 4, 5, 6, 7, 8, 9, 10, 11, or 12, amino acid sequence having at least 99% sequence identity to any one of SEQ ID NO. 1, 2, 3, 4, 5, 6, 7, 8, 9, 10, 11, or 12, or amino acid sequences having 100% sequence identity to the amino acid sequence of SEQ ID Nos. 1, 2, 3, 4, 5, 6, 7, 8, 9, 10, 11, or 12.

In one embodiment, the vaccine composition comprising at least four peptides, wherein the at least four peptides of KRAS comprise the amino acid sequence of SEQ ID NO:1 (P5-21WT: KLVVVGAGGVGKSALTI), SEQ ID NO:4 (P17: SALTIQLIQNHFVDE), SEQ ID NO:6 (P78: FLCVFAINNTKSFED) and SEQ ID NO:8 (P156: FYTLVREIRKHKEKM), an amino acid sequence having at least 70% sequence identity to SEQ ID NO.1, SEQ ID NO:4, SEQ ID NO:6 and SEQ ID NO:8; an amino acid sequence having at least 80% sequence identity to SEQ ID NO.1, SEQ ID NO:4, SEQ ID NO:6 and SEQ ID NO:8, an amino acid sequence having at least 90% sequence identity to SEQ ID NO.1, SEQ ID NO:4, SEQ ID NO:6 and SEQ ID NO:8, an amino acid sequence having at least 95% sequence identity to SEQ ID NO.1, SEQ ID NO:4, SEQ ID NO:6 and SEQ ID NO:8, or an amino acid sequence having at least 99% sequence identity to SEQ ID NO.1, SEQ ID NO:4, SEQ ID NO:6 and SEQ ID NO:8.

In another embodiment, the vaccine composition comprising at least four peptides, wherein the at least four peptides of KRAS comprise the amino acid sequence of SEQ ID NO:1 (P5-21WT: KLVVVGAGGVGKSALTI), SEQ ID NO:2 (P5-21G12D: KLVVVGADGVGKSALTI), SEQ ID NO:4 (P17: SALTIQLIQNHFVDE), and SEQ ID NO:6 (P78: FLCVFAINNTKSFED), an amino acid sequence having at least 70% sequence identity to SEQ ID NO.1, SEQ ID NO:4, SEQ ID NO:6 and SEQ ID NO:8; an amino acid sequence having at least 80% sequence identity to SEQ ID NO.1, SEQ ID NO:2, SEQ ID NO:4 and SEQ ID NO:6, an amino acid sequence having at least 90% sequence identity to SEQ ID NO.1, SEQ ID NO:2, SEQ ID NO:4 and SEQ ID NO:6, an amino acid sequence having at least 95% sequence identity to SEQ ID NO.1, SEQ ID NO:2, SEQ ID NO:4 and SEQ ID NO:6, or an amino acid sequence having at least 99% sequence identity to SEQ ID NO.1, SEQ ID NO:2, SEQ ID NO:4 and SEQ ID NO:6.

In another embodiment, the vaccine composition comprises multiple peptides, e.g. at least 1 peptide, at least 2 peptides, at least 3 peptides, at least 4 peptides, and can comprise any combination of peptides from SEQ ID Nos.1-12, including any amino acid sequences that have at least 70% identity with any one of SEQ ID Nos. 1-12. For example, a particular composition may contain peptides comprising SEQ ID NO: 4, SEQ ID NO: 6 and SEQ ID NO: 8. It is to be understood that the vaccine composition may comprise a combination of two or more peptides selected from Table 1, including SEQ ID Nos. 1-12 in any combination or including vectors encoding the polypeptides or comprising the nucleic acid sequences found in Table 1, for example SEQ ID Nos. 13-24. For example, a suitable composition may contain the peptide of SEQ ID NOs:1, 5, 7 and 9 (or vectors containing the nucleic acids encoding these vectors); alternatively SEQ ID NOs 2, 5, 7, and 9, alternatively, SEQ ID NOs 3, 5, 7 and 9, alternatively SEQ ID Nosi, 4, 6 and 8, alternatively SEQ ID Nos. 2, 4, 6, 8, alternatively SEQ ID Nos. 3, 4, 6, and 8, alternatively SEQ ID Nos. 3, 5, 7, and 9, and so forth and is not limited by the examples described herein.

TABLE 1

| AA Sequence | nucleotide sequence | Homology (mouse vs human) (%) | Immune response |
|---|---|---|---|
| P5-21WT: KLVVVGAGGVGKSALTI (SEQ ID NO: 1) | AAGCTGGTGGTGGTGGGCGCCGGCGGCGT GGGCAAGAGCGCCCTGACCATC (SEQ ID NO: 13) | 100% | Yes |
| P5-21G12D: KLVVVGADGVGKSALTI (SEQ ID NO: 2) | AAGCTGGTGGTGGTGGGCGCCGACGGCGT GGGCAAGAGCGCCCTGACCATC (SEQ ID NO: 14) | 100% | Yes |
| P5-21G12V: KLVVVGAVGVGKSALTI (SEQ ID NO: 3) | AAGCTGGTGGTGGTGGGCGCCGTGGGCG TGGGCAAGAGCGCCCTGACCATC (SEQ ID NO: 15) | 100% | Yes |
| P17: SALTIQLIQNHFVDE (SEQ ID NO: 4) | AGCGCCCTGACCATCCAGCTGATCCAGAA CCACTTCGTGGACGAG (SEQ ID NO: 16) | 100% | Yes |

TABLE 1-continued

| AA Sequence | nucleotide sequence | Homology (mouse vs human) (%) | Immune response |
|---|---|---|---|
| P16: kSALTIQLIQNHFVDEyd (SEQ ID NO: 5) | AAGAGCGCCCTGACCATCCAGCTGATCCA GAACCACTTCGTGGACGAGTACGAC (SEQ ID NO: 17) | 100% | Yes |
| P78: FLCVFAINNTKSFED (SEQ ID NO: 6) | TTCCTGTGCGTGTTCGCCATCAACAACAC CAAGAGCTTCGAGGAC (SEQ ID NO: 18) | 100% | Yes |
| P75: TgegFLCVFAINNTKSFED (SEQ ID NO: 7) | ACCGGCGAGGGCTTCCTGTGCGTGTTCGC CATCAACAACACCAAGAGCTTCGAGGAC [SEQ ID NO: 19) | 100% | Yes |
| P156: FYTLVREIRKHKEKM (SEQ ID NO: 8) | TTCTACACCCTGGTGAGGGAGATCAGGA AGCACAAGGAGAAGATG (SEQ ID NO: 20) | 66.7% | Yes |
| P156HUMAN: FYTLVREIRQYRLKKIS (SEQ ID NO: 9) | TTCTACACCCTGGTGAGGGAGATCAGGCA GTACAGGCTGAAGAAGATCAGC (SEQ ID NO: 21) | 66.7% | |
| p11: AGGVGKSALTIQLLQNHFVD EYD (SEQ ID NO: 10) | GCCGGCGGCGTGGGCAAGAGCGCCCTGAC CATCCAGCTGCTGCAGAACCACTTCGTGG AC GAGTACGAC (SEQ ID NO: 22) | 100% | Yes |
| p11s: AGGVGKSALTIQLLQNHFVD E (SEQ ID NO: 11) | GCCGGCGGCGTGGGCAAGAGCGCCCTGAC CATCCAGCTGCTGCAGAACCACTTCGTGG AC GAG (SEQ ID NO: 23) | 100% | Yes |
| p9: VGAGGVGKSALTIQLLQNHFV DEYD (SEQ ID NO: 12) | GTGGGCGCCGGCGGCGTGGGCAAGAGCGC CCTGACCATCCAGCTGCTGCAGAACCACT TC GTGGACGAGTACGAC (SEQ ID NO: 24) | 100% | Yes |

The vaccine composition suitably include at least one adjuvant. The term "adjuvant" refers to compounds that, when administered to an individual or tested in vitro, increase the immune response to an antigen in the individual or test system to which the antigen is administered.

The adjuvant utilized in methods and compositions of the present invention include, but are not limited to, adjuvants known in the art. Suitable adjuvants include, but are not limited to, a CpG-containing nucleotide sequence, a CpG-containing oligonucleotide, ODN 1826, an aluminum salt adjuvant which are well known in the art and are described, for example, in Harlow, E. and D. Lane (1988; Antibodies: A Laboratory Manual Cold Spring Harbor Laboratory) and Nicklas, W. (1992; Aluminum salts. Research in Immunology 143:489-493), a Montanide ISA adjuvant, a trimer of complement component C3d, MF59, a granulocyte/macrophage colony-stimulating factor (GM-CSF) protein, saponin QS21, monophosphoryl lipid A (MPL), SBAS2, an unmethylated CpG-containing oligonucleotide, an immune-stimulating cytokine, a quill glycoside, a mixture comprising a bacterial mitogen, a mixture comprising a bacterial toxin, a mixture of 2 of the above adjuvants, a mixture of 3 of the above adjuvants or other combinations thereof.

Specifically, suitable adjuvants for human administration include, but are not limited to, for example, GM-CSF, cyclic dinucleotide (CDN), Aluminum, monophosphoryl lipid A (MPL), and STING ligands (cGAMP). The vaccine composition may further comprises a pharmaceutically acceptable carrier. The pharmaceutically acceptable carrier is selected on the basis of the selected route of administration and standard pharmaceutical practice. The composition may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, solutions, parenteral solutions, or suspensions.

Doses, methods of administration, and suitable pharmaceutically acceptable carriers, diluents and excipients can readily be determined by the skilled artisan.

Therapeutically effective amounts of the peptides of the instant invention are combined with a pharmaceutically acceptable carrier to provide a vaccine composition. The composition can be administered in any of the art-recognized modes including orally, mucosally and parenterally, preferably intramuscularly and intravenously. One another aspect of the invention is to provide vaccine compositions that elicit strong immunological anti-tumor response when administered parenterally, preferably intradermally, intramuscularly or sub-cutaneously in mammals preferably in humans. In some aspects, the vaccine compositions are effective when administered mucosally and by other routes such as oral routes or aerosol routes.

Appropriate dosages are determinable for example by extrapolation from animal studies or in clinical trials taking into account body weight of the patient, absorption rate, half-life, disease severity and the like. The number of doses and course of treatment may vary from individual to individual. In some embodiments, for the prevention of the development or progression of cancer, dosages may be required periodically to boost the immune response to the tumor cells. Suitable booster schedules are able to be determined by a skilled artisan. For example, the vaccine may be given every month, every other month, every 4 months, every 6 months, once a year, once every two years, and any range of time in between. Further, the timing and dosages of additional therapies to be delivered with the vaccine can vary and depend on the additional therapy.

For parenteral administration, the peptides or vectors may be mixed with a suitable carrier or diluent such as water, an oil (e.g., a vegetable oil), ethanol, saline solution (e, g., phosphate buffer saline or saline), aqueous dextrose (glucose) and related sugar solutions, glycerol, or a glycol such as propylene glycol or polyethylene glycol. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorobutanol. The composition for parenteral administration may take the form of an aqueous or nonaqueous solution, dispersion, suspension or emulsion.

The composition is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In some aspects, the composition can comprise an isolated and purified plasmid or vector comprising the nucleic acid sequences encoding a KRAS peptide. In some embodiments, the vector comprises the nucleic acid sequence selected from the group consisting of SEQ ID NO: 13-24 operably linked to a transcriptional regulatory element. In some embodiments, the vector or plasmid may encode for one or more of the peptides described herein. Suitable methods of making plasmids or vectors encoding one or more plasmids are known in the art. Suitable compositions may include one or more plasmids or vectors described herein.

In one embodiment, the disclosure provides a vector comprising an isolated and purified nucleic acid sequence comprising at least one nucleic acid sequence encoding at least one peptide selected from the group consisting of SEQ ID Nos. 1-12 or an amino acid sequence having at least 70% sequence identity to SEQ ID Nos. 1-12 operatively linked to a transcriptional regulatory element.

In some embodiments, the vector further comprises heterologous nucleic acid sequence. By "heterologous nucleic acid sequence" we are referring to a non-human nucleic acid sequence, for example, a bacterial, viral, or other non-human nucleic acid sequence that is not naturally found in a human and allows for the expression of the encoded peptide. For example, expression vectors or plasmids are known in the art and contain non-human nucleic acid sequence, including, for example, expression plasmids including CMV promoters.

In some embodiments, the vectors comprise the nucleic acid sequence selected from the group consisting of SEQ ID NO: 13, 14, 15, 16, 17, 18, 19, 20, 21, 22, 23, 24 and combinations thereof and a heterologous nucleic acid sequence.

In some aspects, methods of eliciting an anti-tumor immune response in a subject in need thereof are provided. The method comprises administering an effective amount a vaccine composition provided herein to the subject, wherein the vaccine composition elicits an anti-tumor immune response. In some embodiments, the anti-tumor immune response is a MHC class II mediated T cell response. This increased anti-tumor immune response reduces the number of tumor cells in a subject or tumor size in the subject. In some aspects, the anti-tumor response results in the prevention of tumor cell growth and leads to tumor cell apoptosis. In some aspects, the MHC class II mediated T cell response is a CD4+ T cell response.

In other aspect, methods of treating cancer or methods of reducing, inhibiting or preventing cancer cell growth are provided. The methods comprise administering an effective amount of the vaccine composition provided herein, including, for example, a vaccine composition comprising at least one peptide of KRAS, suitably at least two peptides of KRAS, wherein the effective amount is able to treat cancer or inhibit, reduce or prevent cancer cell growth, proliferation, invasiveness or metastasis in the patient.

In some aspects, the vaccine compositions can be used to selectively increase the cell death of tumor cells within a patient, leading to a reduction in the size of tumors, inhibition of tumor growth and/or reduction or inhibition of metastasis.

In some aspects, method of treating cancer comprises administering the vaccine composition prior to, concurrently with, or after treatment with standard therapies. Suitable standard therapies include, but are not limited to, surgery, radiation therapy (RT), and chemotherapy (CT), among others.

In some aspects, the vaccine composition is administered in an effective amount increasing efficacy of radiotherapy or chemotherapy in the treatment of cancer in a patient. Suitable modes of chemotherapy are known by one skilled in the art.

The methods disclosed herein can include a conventional treatment regimen, which can be altered to include the steps of the methods described herein. The methods disclosed herein can include monitoring the patient to determine efficacy of treatment and further modifying the treatment in response to the monitoring.

In further aspects, methods of preventing, reducing or slowing the progression or development of cancer in a patient at risk of developing a KRAS-associated cancer are provided. The method may comprise determining if a patient is at risk of developing a KRAS associated cancer; and treating the patient with an effective amount of the vaccine composition provided herein.

Method of determining if a patient is at higher risk for developing a KRAS associated cancer are known in the art, for example, by detecting a mutation of KRAS in a sample from a patient. It has been shown that KRAS mutations can be found in the circulating free DNA (cfDNA) of non-small cell lung cancer (NSCLC) patients. Methods of detecting this circulating free DNA are known in the art, as described in Garzon et al. "KRAS mutations in the circulating free DNA (cfDNA) of non-small cell lung cancer (NSCLC) patients" *Transl Lung Cancer Res* 2016; 5(5):511-516, which is incorporated by reference in its entirety. Suitable methods include, but are not limited to, Real-time PNA PCR and other standard techniques.

The detecting of the mutation of KRAS from a sample is suitably a biological sample, for example, a tissue sample from a biopsy or a fluid sample, for example, a blood sample.

In some embodiments, the methods further comprise administering at least one checkpoint inhibitor.

Accordingly, in one embodiment, the present invention provides a method of treating cancer or initiating, enhancing, or prolonging an anti-tumor response in a subject in need thereof comprising administering to the subject a vaccine composition in combination with an agent that is a checkpoint inhibitor. In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof.

In one embodiment, the checkpoint inhibitor is an anti-PDL1 antibody, an anti-TIM3 antibody, and anti-VISTA antibody, an anti-CTLA-4 antibody or a combination thereof.

In another embodiment, the checkpoint inhibitor is a PD-1/PD-L1 peptide vaccine comprising a peptide of PD-1 or PD-L1. In another embodiment, the PD-1/PD-L1 peptide vaccine comprises at least one peptide from Table 3 or 4, or an amino acid sequences having at least 70% sequence identity to any one of SEQ ID NO. 33-54, alternatively an amino acid sequences having at least 85% sequence identity to any one of SEQ ID NO. 33-54, alternatively an amino acid sequences having at least 90% sequence identity to any one of SEQ ID NO.33-54, alternatively an amino acid sequences having at least 95% sequence identity to any one of SEQ ID NO. 33-54, alternatively an amino acid sequences having at least 98% sequence identity to any one of SEQ ID NO. 33-54, alternatively an amino acid sequence having at least 99% sequence identity to any one of SEQ ID NO. 33-54, or alternatively an amino acid sequences having 100% sequence identity to the amino acid sequence of SEQ ID Nos. 33-54.

In some embodiments, the at least one K-ras peptide, alternatively at least two K-ras peptides, alternatively at least three K-ras peptides, alternatively at least 4 K-ras peptides is combined with at least at least one PD-1/PD-L1 peptide, alternatively at least two PD-1/PD-L1 peptides, alternatively at least three PD-1/PD-L1 peptides, alternatively at least four PD-1/PD-L1 peptides found in Table 3 or 4, or any amino acid having at least 70% sequence identity to any one of the peptides found in Table 3 or 4, alternatively at least 80% sequence identity to any one of the peptides found in Table 3 or 4, alternatively at least 90% sequence identity to any one of the peptides found in Table 3 or 4.

In one embodiment, the K-ras peptides and the PD-1/PD-L1 peptides are combined into a single vaccine formulation. In some embodiments, the at least one K-ras peptide, alternatively at least two K-ras peptides, alternatively at least three K-ras peptides, alternatively at least 4 K-ras peptides is combined with at least at least one PD-1/PD-L1 peptide, alternatively at least two PD-1/PD-L1 peptides, alternatively at least three PD-1/PD-L1 peptides, alternatively at least four PD-1/PD-L1 peptides.

In some embodiments, the vaccine composition and checkpoint inhibitor are administered simultaneously. In other embodiments, the vaccine composition and checkpoint inhibitors are administered sequentially, with, minutes, hours or days in-between treatment. Suitable schedules for administration can be determined by a skilled practitioner.

In another aspect, the present invention provides a method of treating or preventing cancer or initiating, enhancing, or prolonging an anti-tumor response in a subject in need thereof comprising administering the vaccine composition in combination with an RXR agonist. Suitable RXR agonist are known in the art and include, but are not limited to, for example, bexarotene, UAB30, and low dose retinoic acid (e.g. 25-300 µg/mouse/day). For example, low dose retinoic acid for a human subject includes about 45 to 100 mg/m2/day. For example, suitable dosages of bexarotene for a human subject may be from about 75 mg/day to about 200 mg/day, suitably about 150 mg/day. Suitable dosages of UAB30 for a human subject include, for example, about 75 mg to about 300 mg per day, suitably about 200 mg to about 300 mg/day.

In another aspect, the present invention provides a method of treating cancer or initiating, enhancing, or prolonging an anti-tumor response in a subject in need thereof comprising administering the vaccine composition in combination with a nonsteroidal anti-inflammatory drug (NSAIDs) in an effective amount to treat or prevent cancer or to enhance or prolong the anti-tumor response in a subject. It has been demonstrated that the use of a NSAIDs, e.g. cox inhibitor, synergistically enhances the anti-tumor effect of a vaccine. See Selene et al. "Cyclooxygenase-Dependent Tumor Growth through Evasion of Immunity" 2015, *Cell* 162, 1257-1270, incorporated by reference in its entirety.

In another aspect, the present invention provides a method of treating or preventing cancer or initiating, enhancing, or prolonging an anti-tumor response in a subject in need thereof comprising administering the vaccine composition in combination with avasimibe (CI-1011), an inhibitor of acyl coenzyme A-cholesterol acyltransferase (ACAT). Suitable dosages of avasimibe are known in the art and include, but are not limited to, for example, 50 mg day to about 1000 mg/day, alternatively about 50 mg/day to 500 mg/day, for example, 50 mg/day, 125 mg/day, 250 mg/day or 500 mg/day.

Aspects of the disclosure described with respect to the former method can be applicable to the latter method, and vice versa, unless the context clearly dictates otherwise.

The term "subject" and "patient" are used interchangeably herein and refer to a mammal or animal in need of treatment. Suitable subjects include, mammals, including, for example, humans, dogs, cats, horses, cows, rats, mice, monkeys. In a preferred embodiment, the subject is a human.

The terms "effective amount" or "therapeutically effective amount" refer to an amount sufficient to effect beneficial or desirable biological and/or clinical results.

Suitable kits are also included for preforming the methods described herein. Kits may comprises a vaccine composition as described herein and instructions for the administration of the vaccine composition.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

EXAMPLES

Example 1 demonstrates the use of peptides to KRAS described herein. Specifically, this Example demonstrates a multipeptide KRAS vaccine was immunogenic and efficacious in the primary prevention of KRAS-induced lung cancer.

Lung cancer remains the leading cause of cancer death worldwide. Mutations in KRAS are detected in up to 30% of lung cancer cases. No effective therapies specifically targeting mutant KRAS have been developed. Boosting the host immune response by vaccinating against defined tumor-associated antigens as a means of treating established tumors or preventing the development of tumors in high-risk individuals is an area of intense research. The present study evaluated both immunogenicity and antitumor efficacy of a newly formulated multipeptide vaccine targeting multiple epitopes of the KRAS molecule in a mouse model of a KRAS-driven lung tumor. The formulated vaccine contained top four peptides, which elicited the strongest immunologic response and showed 100% sequence homology between human and mouse. The multipeptide KRAS vaccine was tested in an inducible CCSP-TetO-KRAS$^{G12D}$ mouse model, where the vaccines were administered prior to activating the mutant KRAS protein. The KRAS peptide vaccine exhibited striking efficacy, reducing tumor number and tumor burden by >80% when compared with adjuvant alone. Splenocytes collected from vaccinated animals showed a robust immunologic response to the immunizing peptides. Furthermore, in vitro stimulation of these splenocytes by the vaccinated peptides resulted in the secretion of cytokines indicative of Th1 and Th17 responses but with minimal secretion of Th2-related cytokines. The multipeptide KRAS vaccine was immunogenic and efficacious in the primary prevention of KRAS-induced lung cancer, indicating that the approach potentially can be used to prevent other KRAS-driven cancers, either alone or in combination with other modalities.

Material & Methods

Mice

Inducible TetOKRAS mice expressing murine KRAS with G12D mutation on FVB background were obtained from the NCI Mouse Models Consortium, and were then crossed with mice expressing the Tet-on Clara Cell Secreted Protein (CCSP) on the A/J background to permit tissue specific inducible expression of the transgene. For all experiments reported herein, only the F1 generation that harbor both KRAS$^{G12D}$ and CCSP were used. All mice were housed in the Biomedical Resource Center at the Medical College of Wisconsin, Milwaukee, WI. All procedures were approved by the institutional animal care and use committee (IACUC).

Scoring System for the Prediction of MHC Class II Binding Epitopes

We and others have shown that peptides that score highly across multiple algorithms are most likely to yield strong immune responses. Therefore, we used the same multi-scoring system as previously described [13]. Briefly, to identify KRAS-specific MHC class II epitopes that have optimal binding affinity and promiscuity across multiple alleles, the following algorithms were used for prediction: SYFPEITHI (Institute for Cell Biology, Heidelberg, Germany), IEDB, and Rankpep (Harvard, Boston, MA).

Figures 1A, 1B, 1C:
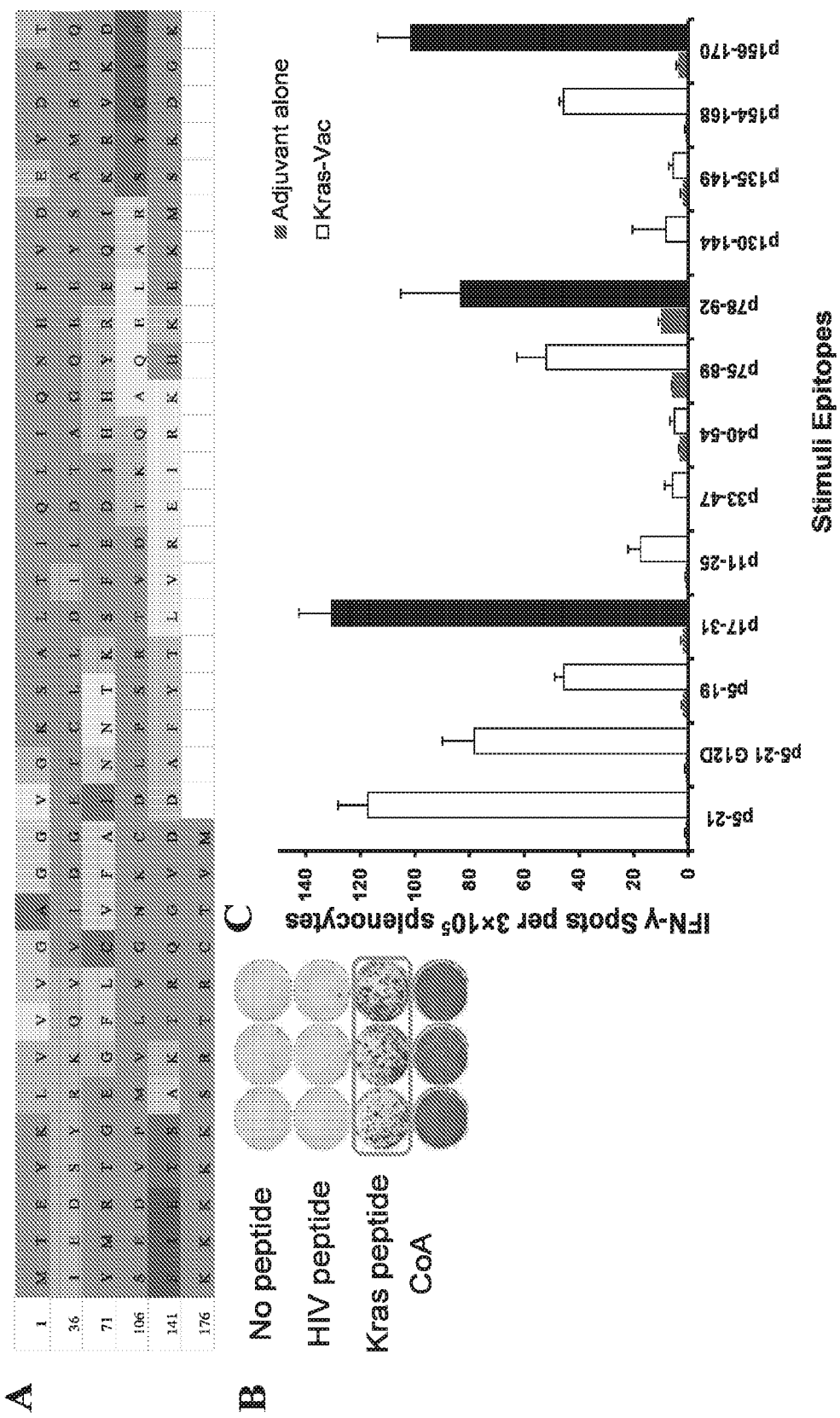
FIG. 1A-1C. In vivo screen for peptide candidates by ELISPOT in naïve mice. (A) Immunogenic heatmap for identifying peptides associated with highest binding affinity across multiple MHC class II alleles. Colors represent percentile to highest score from three algorithms for each amino acid from dark red to light blue in the order of rank scores. Color strata are as follows: dark red 75% of the highest score; red=50~75% of the highest score; orange=40~50% of highest score; yellow=30~40% of the highest score; green=20~30% of the highest score; blue ≤20% of the highest score. (B) Representative ELISPOT results showing T cell responses to specific KRAS peptides from mouse splenocytes stimulated with no antigen (first row), negative control peptide (HIV peptide, second row), target peptide (third row), or positive control ConA (fourth row). (C) Quantified ELISPOT results. Mice were vaccinated with each single KRAS peptide (sequence listed in Table 2). Then, splenocytes were collected and pulsed with no antigen control, each single KRAS peptide, or negative control peptide (HIV peptide), or positive control ConA. After 72 h of incubation, the ELISPOT assay was performed, plates were scanned, and spot numbers were statistically analyzed. Open bar, ELISPOT reads from KRAS peptide vaccinated animals pulsed with specific KRAS peptide; blue bar, ELISPOT reads from animals injected only with adjuvant and pulsed with specific KRAS peptide; black bar, ELISPOT reads from three most significant KRAS peptide vaccinated animals. Data are shown as the mean±SE of three replicate wells per group, n=5.

The 11 peptides described in this study were selected as follows. For each available MHC Class II allele from the 3 algorithms, 20 peptide sequences were initially selected solely on the basis of the rank order of the predicted binding affinity. The sequences are approximately 15 amino acids in length. Individual amino acids for each selected peptide were assigned a score, with 1 being an amino acid contained in a peptide sequence that ranked highest for predictive binding affinity across multiple algorithms. Scoring individual amino acids accounted for the multiple peptides overlaps occurring within and across algorithms. The scores (S) for each amino acid were summed up across the multiple MHC Class II alleles from all 3 algorithms. Then, the number (N) of MHC class II alleles, for which each amino acid was predicted to have high affinity binding, was counted. The final score for each amino acid was calculated by multiplying S and N. For ease of identifying the most potentially immunogenic segments of the KRAS protein, each amino acid was assigned a color (from dark red to light blue) based on its final score percentile, with dark red being highest at ≥75% and light blue the lowest at <10% (FIG. 1A). Thus, the dark red color corresponds to a sequence where multiple peptides scored highly within an algorithm as well as across algorithms. Light blue represents sequences that are the least potentially immunogenic of all predicted high binding peptides. KRAS peptides were synthesized by Genemed Synthesis Inc. (South San Francisco, CA), purified by high-performance liquid chromatography, and characterized by mass spectrometry for use in all experiments.

Vaccine Preparation and Immunization

Figures 2A, 2B, 2C, 2D, 2E, 2F, 2G, 2H:
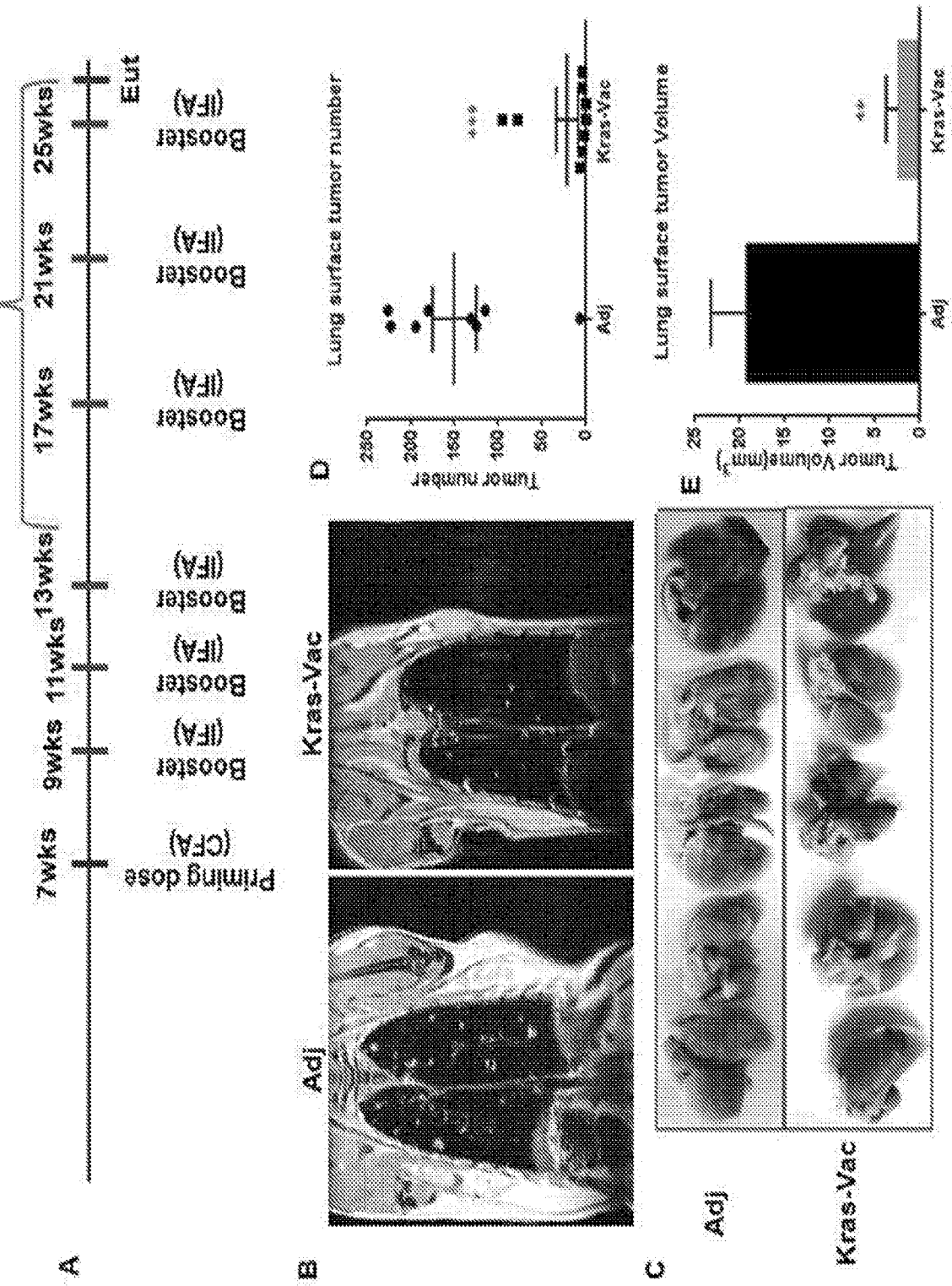
FIG. 2A-2H. KRAS vaccine inhibited KRASG12D-driven mice in conditional CCSP-KRAS mice in prevention setting. (A) Schematic of the experimental design outlining timing of vaccine administration, induction of the oncogenic transgene, imaging time points, and experimental endpoint. (B) Representative MRI images from mice injected with either adjuvant control or KRAS multipeptide vaccine. Quantification of surface tumor. Typical lung lobes with surface tumors from each group (C), surface tumor number (D), and tumor volume quantitation (E). (F) Representative lung lobes (H&E slides) to show tumors inside lungs from each group, illustration of tumor counting. Inside tumor number (G) and tumor volume quantitation (H). Data are shown as the mean±SE, n=8 (adj), n=9 (KRAS-Vac), $*P \leq 0.05$, $P \leq 0.01$, $*P \leq 0.001$, $****P \leq 0.0001$ FIG. 3. Epitope spreading tested by IFN-γ ELISPOT. Mice were vaccinated with the KRAS combination vaccine (p5-21, p5-21 G12D, p17-31, and p78-92). Then splenocytes were collected and pulsed with KRAS combo peptides, each single KRAS peptide, unvaccinated KRAS peptide p75-89, combo IGFR peptides, or Tert peptide. After 72 h of incubation, the ELISPOT assay was performed, plates were scanned, and spot numbers were statistically analyzed.
Figures 2A, 2B, 2C, 2D, 2E, 2F, 2G, 2H:
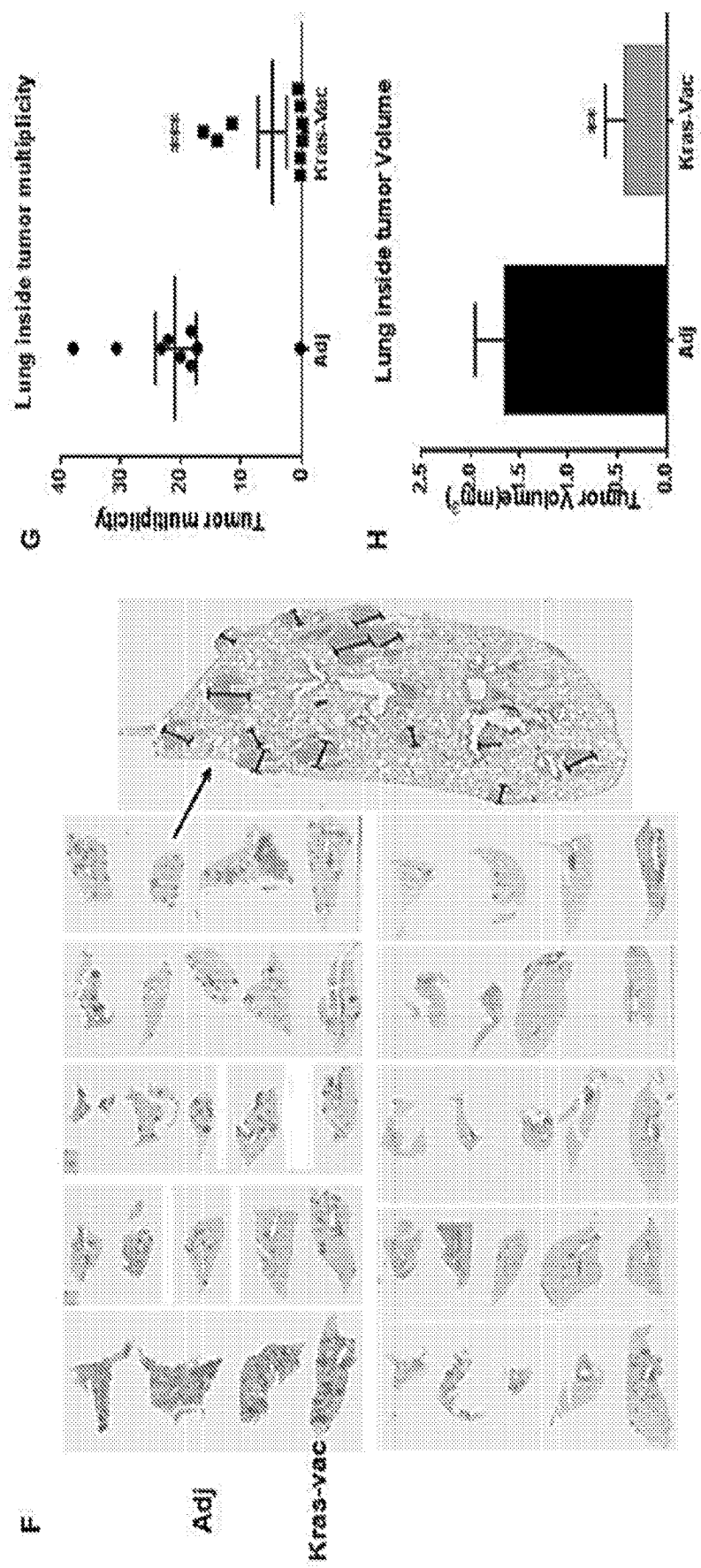

Mice were vaccinated with 50 μg of each peptide. Phosphate buffered saline (PBS) was added to bring the total volume to 50 μL/mouse. An equal amount of adjuvant (Complete Freund's Adjuvant or Incomplete Freund's Adjuvant) was added to bring the total volume to 100 μL/mouse. Mice were injected subcutaneously on the shoulder at 7 weeks of age, and boosting vaccination was given every two weeks for the first three boosting and every 4 weeks for the last three boosting as shown in FIG. 2A. Transgene Kras was initiated with Dox diet (625 mg/kg diet) one week after the fourth vaccination, and Dox diet was given throughout of the study.

ELISPOT Assay

Cell suspensions from whole spleens were filtered through a 70 μm cell strainer (BD) and subjected to red blood cell lysis using ACK lysis buffer. 1.5~3.0×10$^4$ cells were plated into individual wells of a MAIPS4510 Multi-screen 96 well plate previously coated with anti-interferon γ detection antibody and containing media with either peptide, positive control (concanavalin A) or negative control (HIV peptide, or no antigen). After 72 hours, plates were washed and a secondary antibody (BD) was added and incubated on the plate overnight at 4 degrees Celsius. Wells were then washed with PBS and HRP streptavidin was added. Following 1 h incubation, the plate was developed using AEC substrate for between 5-25 minutes. The plate was subsequently gently washed under cold running tap water. When dry, an automated plate reader system (CTL Technologies) was used to image the plates and quantify spot number.

Magnetic Resonance Imaging

Mice were imaged using a 9.4T MRI (Bruker, Billerica, MA) with a custom birdcage style quadrature coil (Doty Scientific, Columbia, SC). Mice were anesthetized with isoflurane for the duration of the imaging procedure. Mice were induced at 2.5% isoflurane and maintained at 1.0-1.5%. Mouse heart rate, body temperature and respiratory rate were continuously monitored throughout imaging. Both respiratory and cardiac gating using an electrocardiogram were used to ensure that images were consistently acquired during latent periods of the respiratory cycle and at a consistent point during the cardiac cycle. Tumors were imaged using a multi-slice, multi-echo acquisition (MSME). Images were acquired using the following parameters; TE=8.07 ms, TR≥400 ms (variable), matrix=128×128, 1 average, 20 axial slices.

Lung Tumor Counting Using H&E Staining

Mouse lung samples from CCSP-KRASG12D mice were inflated and formalin fixed and processed (Sakura Tissue Tek VIPS) for paraffin embedding. After paraffin embedding, samples were sectioned at 4 μm (Microm HMS355S) onto poly-1-lysine coated slides and air dried at 45° C. overnight prior to immunohistochemistry or H&E staining.

H&E stained slides were scanned using the NanoZoomer slide scanner (Hamamatsu). Subsequently, NanoZoomer software was used and tumor regions were specifically highlighted and measured. Three slides were selected per mouse for analysis, corresponding to a ventral, midline and dorsal region of the lung.

Flow Cytometry

Mesenchymal lymph nodes, mouse lung or spleen were minced and processed to single cell suspensions. Single cells were evaluated using flow cytometry for expression of surface markers CD4, CD8, CD44, CD62L and CD25 (eBioscience), as well as intracellular staining for FoxP3 (eBioscience). Stained cells were fixed in 1% paraformaldehyde and were permeabilized following the manufacturer's instructions to evaluate the expression of intracellular targets (FoxP3). Flow cytometry was conducted using an LSR-II flow cytometer (BD). Data was analyzed using FlowJo software (Tree Star).

Cytokine Analysis

Mouse Th1/Th2/Th17 Cytokines Multi-AnalyteELISArray™ Kits (Qiagen) were used for cytokine analysis; it analyzes a panel of 12 cytokines involved in T helper cell biology. The cytokines represented by this array are IL2, IL4, IL5, IL6, IL10, IL12, IL13, IL17A, IL23, IFNγ, TNFα, and TGFβ1. Splenocytes from different groups of mice were stimulated with different peptides for 72 h, and then supernatant was collected and assayed based on the manufacturer's instructions.

Evaluation of Tumor-Infiltrating T Cells

Tumors were frozen in Tissue-Tek OCT and stored at −80 C. Frozen tumors were then sectioned (8 mm), fixed in 75%/25% acetone/methanol for 5 minutes, and washed using PBS. Slides were incubated with normal goat serum (10% in PBS) for 1 hour at room temperature, washed, and incubated with rat anti-mouse CD8 (AbDSerotec) at 1:100 dilution in 10% goat serum/PBS overnight at 4 C. After washing, Alexa Fluor 488 goat anti-rat secondary antibody (Invitrogen) was added to the slides (1:1000) for one hour at room temperature. Prolong Gold antifade with 4', 6-diamidino-2-phenylindole (DAPI) mounting media (Invitrogen) was added after an additional wash and cover slips were attached. Positive cells and DAPI stained nuclei were counted in three random high-powered microscopic fields per slide and expressed as a mean. The number of positive cells in the field was expressed as # of $CD8^+$ cells per $mm^2$ tumor area. Data are shown as the mean and SEM for 3 mice/group.

Statistical Analysis

All in vitro assays were performed at least in triplicate. Five to nine mice per group were used for the in vivo studies. A two-tailed Student's t-test was used to evaluate differences between the control and each treatment group. *$P<0.05$, $P<0.01$, and *$P<0.001$ were considered statistically significant.

Results

Identifying KRAS Peptides that Elicit T Cell Response by a Multi-Scoring System Combining Multiple MHC Class H Peptide Binding Algorithms Using a multi-scoring system that combines multiple MHC class II peptide binding algorithms, immunogenic "hotspots" were identified; 11 peptides (Table 2) were selected; their immunogenicity was evaluated in naïve mice using the IFN-γ ELISPOT assay as previously reported. The KRAS 17-mer peptide (p5-21) that covers the mutation in codon 12, and its G12D mutant (p5-21 G12D) were also selected as robust peptides to stimulate immune response [14]. FIG. 1A demonstrates the entire KRAS protein sequence and the immunogenic "hotspots" identified through the multi-scoring system solely on MHC class II epitopes. Of the 11 newly designed peptides, six of them (45%) were immunogenic, with p5-21, p17-31, p78-92, and p156-170 eliciting the strongest IFN-γ response (FIG. 1C). Interestingly, p75-89, which differed from p78-92 by only three amino acids, yielded a much weaker response in naïve animals. Similarly, p154-168 yielded a much weaker response than p156-170 despite great overlap in the peptides, and p5-19, which is contained within p5-21 with only two amino acids missing in the C-terminus, yielded less than 50% response of p5-21. The two 17-mer peptides (p5-21 and p5-21 G12D mutant) also demonstrated strong immunogenicity with a mean for the IFN-γ-secreting cells of around 100 spots per well (SPW) compared to 10 SPW for the negative control HIV peptides (FIGS. 1B, 1C). As expected, mice immunized with adjuvant alone did not develop any antigen-specific IFN-γ response to either single peptide or multipeptide stimulation, with the mean IFN-γ response similar to that of the HIV peptide ($P<0.0001$, FIGS. 1B, 1C). To include peptides against both wild-type and mutant KRAS, also based on a high degree of homology between human and mouse KRAS, peptides p5-21 (SEQ ID NO:2), p5-21 G12D (SEQ ID NO:1), p17-31 (SEQ ID NO:4), and p78-92 (SEQ ID NO:6) were chosen to formulate a multipeptide KRAS vaccine in the preventive efficacy study.

KRAS-Specific Multipeptide Vaccine Prevents Lung Tumor Formation in Primary Prevention Setting We conducted the experiment in a doxycycline-inducible KRASG12D murine model. As illustrated in FIG. 2A, the first prime vaccination was given with CFA as adjuvant when mice were seven weeks old, followed by three boosting vaccinations administered with IFA at two-week intervals. One week after the last vaccination in IFA, doxycycline was started in diet to induce KRASG12D expression. Additional boosting vaccinations were administered at four-week intervals throughout the rest of the study. Tumor growth was first evaluated in situ with MRI imaging from at least three representative animals just prior to the experimental endpoint. As shown in FIG. 2B, MRI imaging demonstrated significant qualitative differences within the lung parenchyma between non-vaccinated and vaccinated mice. Representative non-vaccinated and vaccinated mouse lungs are shown in FIG. 2C. Lungs from non-vaccinated mice were fully covered with lung adenocarcinoma, whereas lungs from KRAS-specific peptide vaccinated mice appeared virtually free of gross tumors. KRAS vaccine significantly decreased surface tumors from ~150 tumors per mouse lung in non-vaccinated mice to ~21 tumors in vaccinated mice (FIG. 2D), and decreased tumor volume nearly 90% (FIG. 2E, 19.1 $mm^3$ to 2.4 $mm^3$). Further analysis was also done on the internal tumor counting via H&E staining. A representative histological examination of lungs from vaccinated versus adjuvant-treated animals reveals changes within the lung parenchyma (FIG. 2F). Similar to surface tumor counting, vaccinated animals demonstrated an average of ~5 tumors per slide with average volume of 0.4 mm$^3$, as compared to an average of ~21 tumors per slide (p=0.0013) with average volume of 1.6 mm$^3$ in animals not receiving the vaccine (p=0.0043), equating to a 75% reduction in both tumor multiplicity and tumor volume (FIGS. 2G,2H). It is noteworthy that two out of nine vaccinated animals were completely free of lung tumors (FIG. 2G). These results suggest that a KRAS-specific peptides vaccine can inhibit KRAS-driven lung carcinogenesis in prevention setting.

Figure 3:
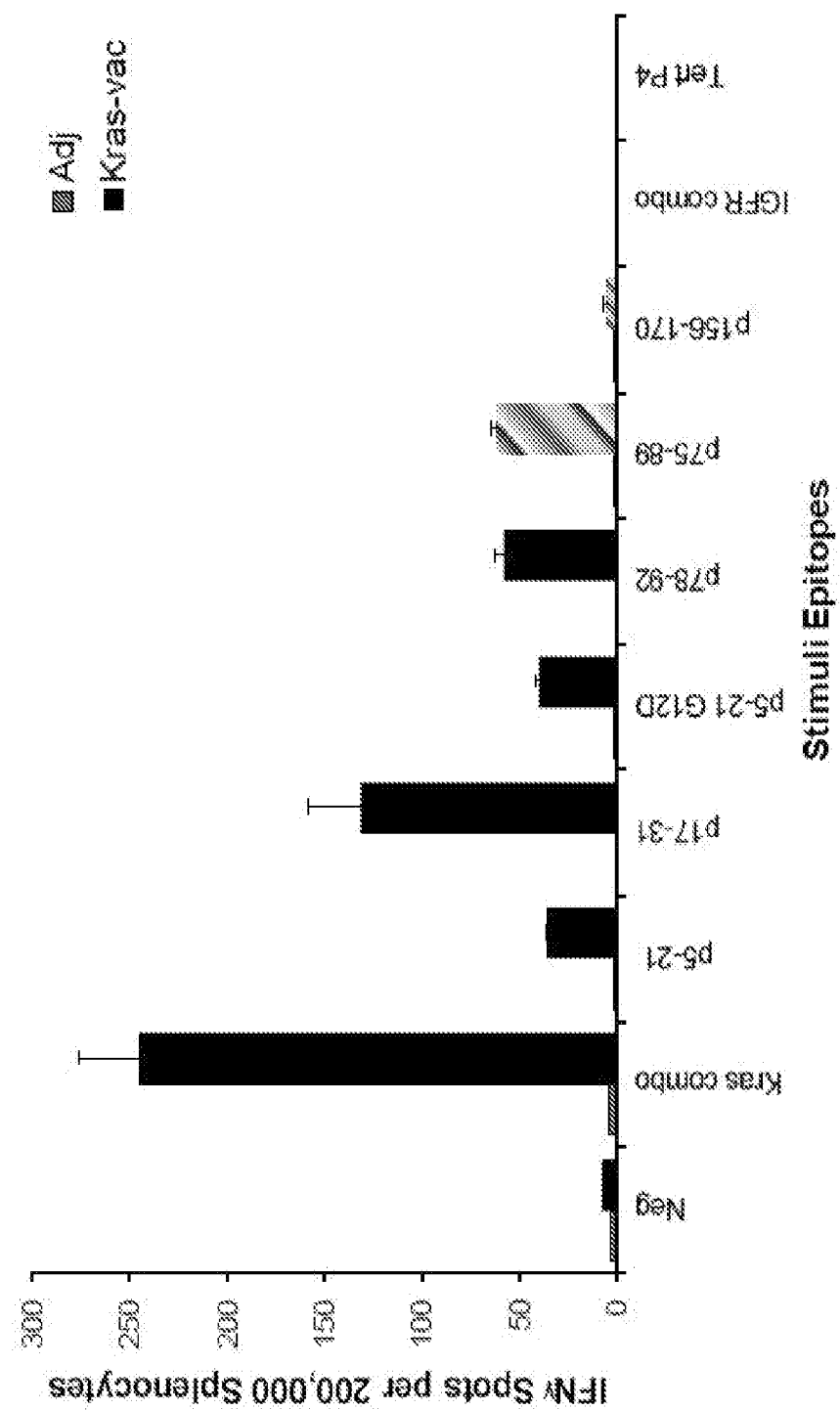

KRAS Vaccination Induces T Cell-Specific Immune Response and Possible Intra-Antigen Epitope Spreading In order to examine the specific immunity that confers the protective effect of the KRAS vaccine, an IFN-γELISPOT assay of splenocytes isolated from adjuvant alone and vaccinated CCSP-KRAS$^{G12D}$ mice was performed at the end of the study. Results from the ELISPOT assay indicated that vaccinated animals had a robust antigen-specific, IFN-γ-associated immune response to the KRAS vaccine. As shown in FIG. 3, splenocytes from the vaccinated mice showed the highest level of IFN-γ response to the mixture of four KRAS peptides used in the vaccine formulation, although they also responded to the individual peptides that constituted the vaccine. The mean IFN-γ-secreting cell responses were 216 in the pooled KRAS peptides group, and 36, 40, 116, and 52 to individual peptides p5-21, p5-21 G12D, p17-31, and p78-92, respectively. Interestingly, we observed that splenocytes from vaccinated animals had a strong response to non-vaccine KRAS peptide p75-89, which has a 12 amino acid overlap with one peptide p78-92 used in the vaccination (p75-89, FIG. 3). This suggests that the current KRAS vaccine may have induced intramolecular epitope spreading. The observed immune response appeared highly specific to the vaccine KRAS peptides, as evidenced by the lack of response in animals that received adjuvant alone; these animals were exposed to the mutated KRAS protein overexpressed in the growing tumor but showed no immunologic reactivity to any peptides tested, including the peptide encompassing the mutant region (p5-21 G12D). There was no evidence of general immune hyperactivity stimulation as none of the animals responded to an irrelevant naïve antigen, further supporting the notion that the immune response detected in the vaccinated group was highly specific to the KRAS vaccine.

Figures 4A, 4B, 4C, 4D, 4E:
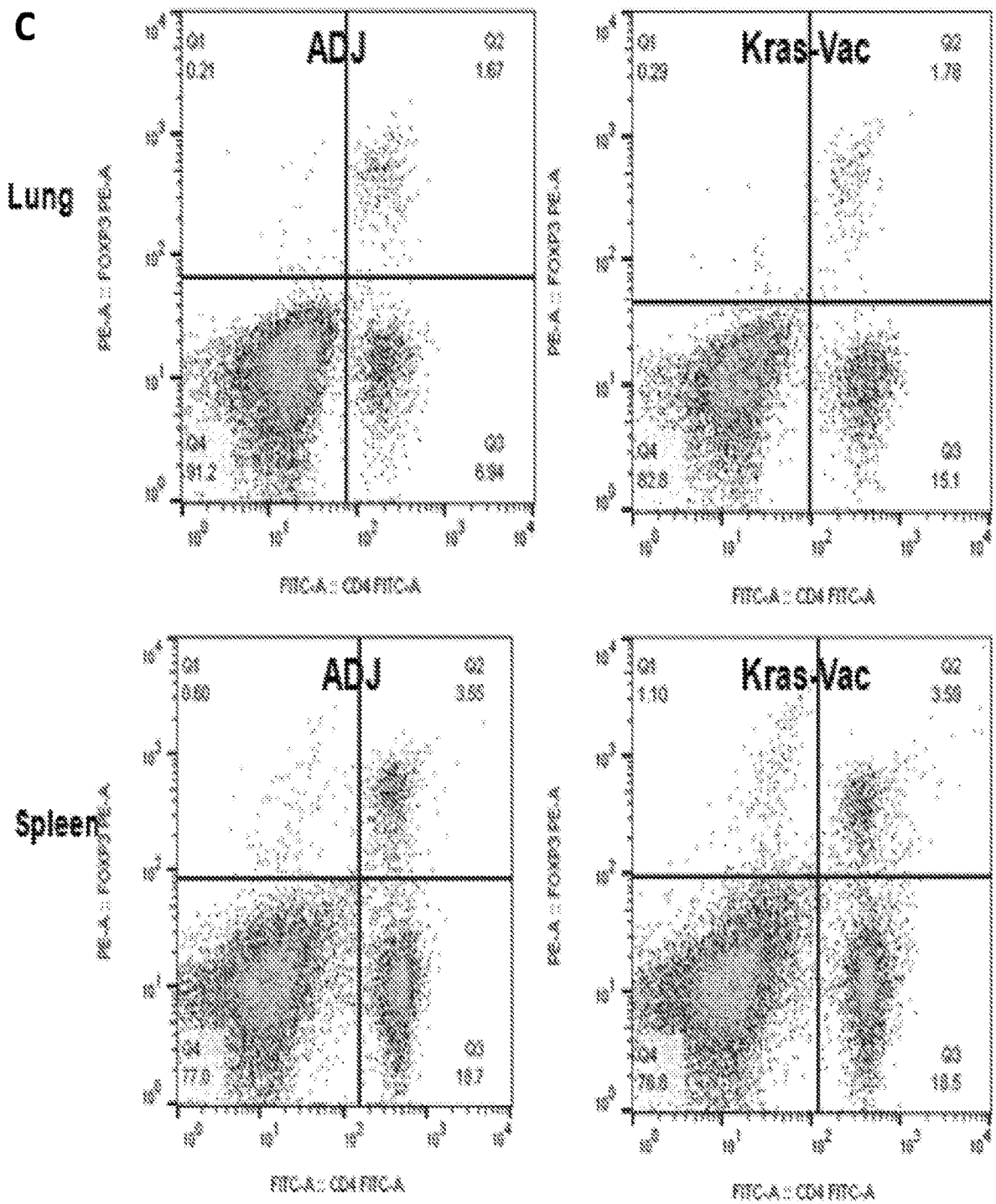
Figures 4A, 4B, 4C, 4D, 4E:
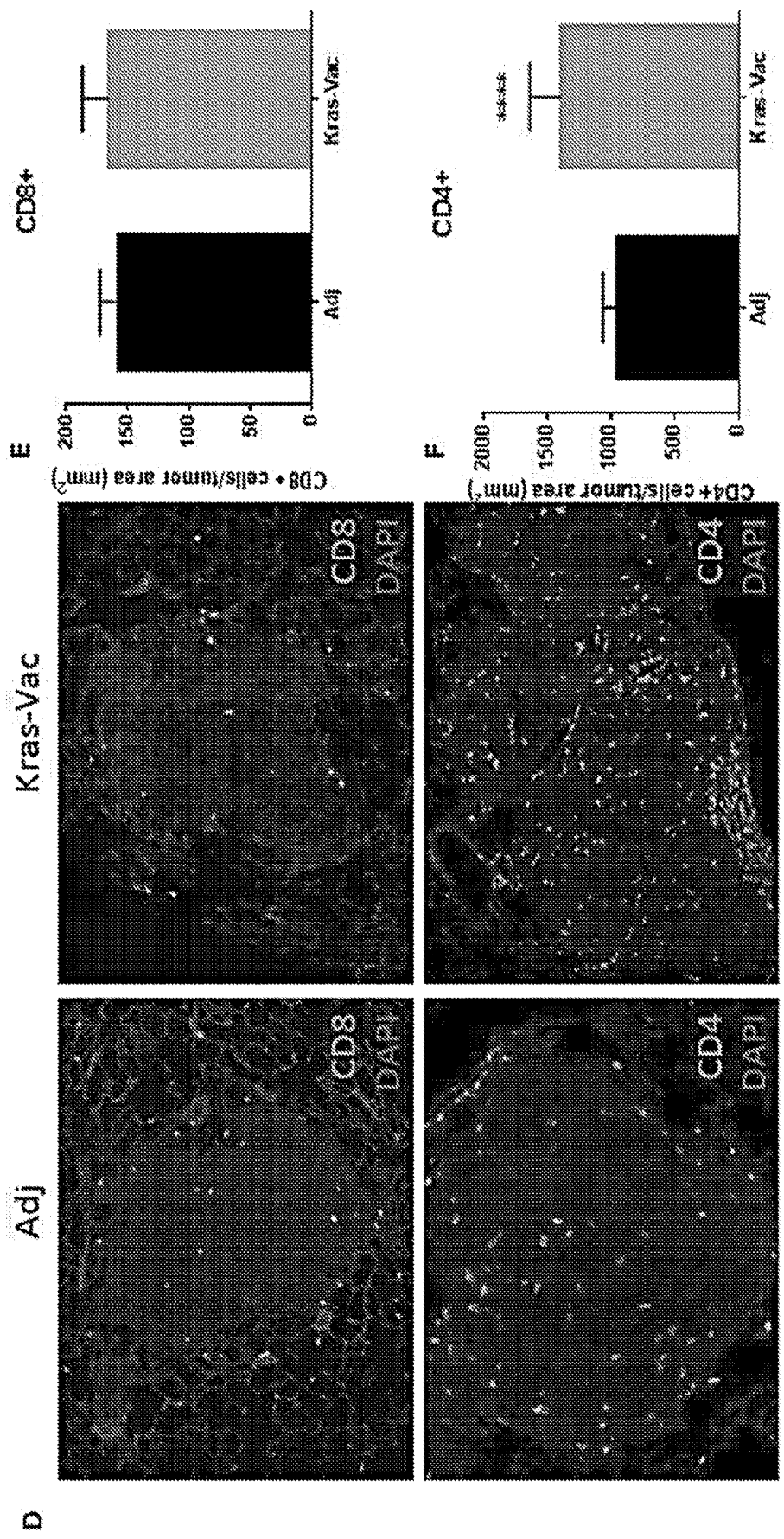

KRAS Vaccination Increases CD4+/CD8+ Cells in Lung Draining Lymph Nodes, as Well as CD4+ Tumor Infiltrating Lymphocytes A detailed flow cytometric analysis of cell surface markers further revealed the differential characteristics of the CD4+ and CD8+ lymphoid populations present both in lymph nodes (FIG. 4A) and the spleen (FIG. 4B). The overall percentage of CD4+ and CD8+ cells within the lung draining lymph nodes from vaccinated animals trended upward (p=0.16 and 0.056, respectively), while the percentage of Tregs that express CD4 and the FoxP3 transcription factor appeared to remain unaffected (FIG. 4C). We further evaluated the number of both CD4+ and CD8+ tumor-infiltrating lymphocytes from representative mice in each group that developed lung cancer (FIGS. 4D, 4E, 4F). The KRAS vaccine significantly increased the number of intra-tumoral CD4+ Tcells over adjuvant controls, while there was no difference in CD8+ tumor-infiltrating lymphocytes cells.

Th1/Th2 Cytokine Profiles of T Cell Responses to Helper Peptide Vaccination

Figure 5:
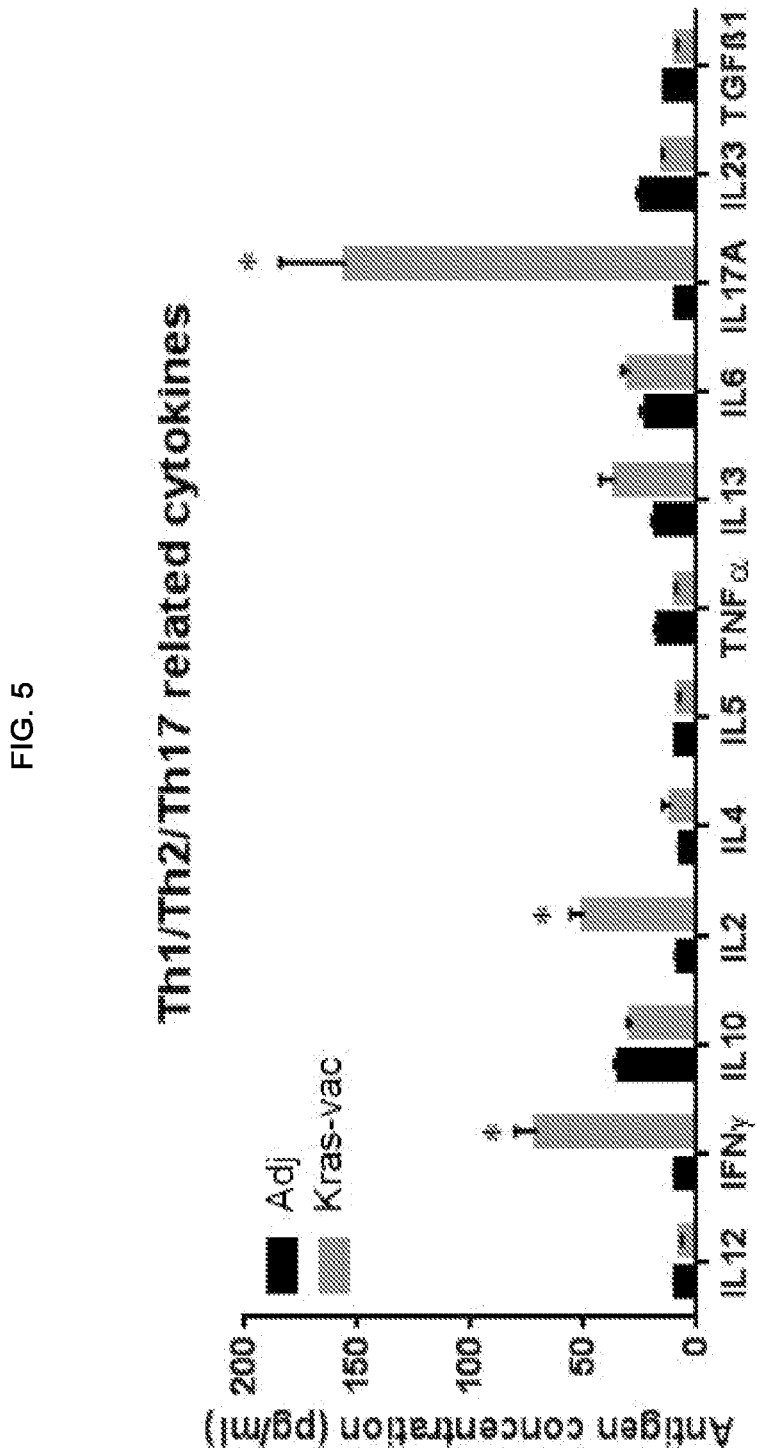
FIG. 5. KRAS vaccine induces Th1/Th17 cytokine response. Cytokine analysis by an ELISArrayKit from QIAGEN. After last boosting vaccination, splenocytes from either KRAS vaccinated or adjuvant alone mice were collected and cocultured with KRAS vaccine for 72 h; supernatant was collected and assayed with QIAGEN's ELISArrayKit follow manufacturer's instruction. Data are shown as the mean±SE, n=8 (Adj), n=9 (KRAS-Vac), $*P \leq 0.05$, $P \leq 0.01$, $*P \leq 0.001$, $****P \leq 0.0001$ FIG. 6. Immunogenic heatmap for human Kras with common 14 MHC class II alleles.
Figure 6:
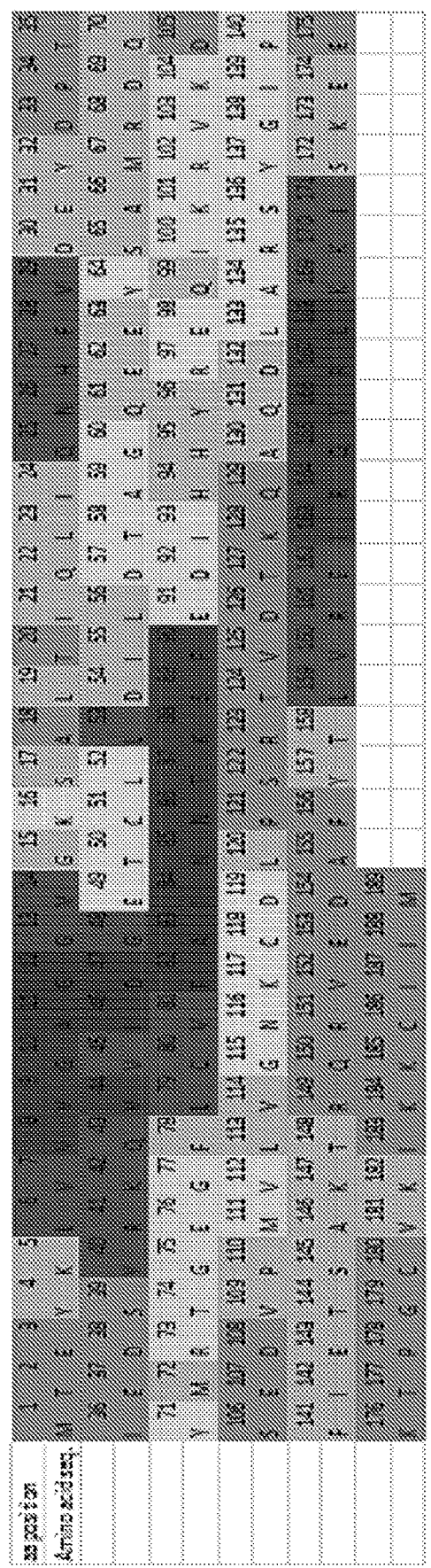

Cytokines secreted by splenocytes were measured three days after in vitro stimulation with the vaccinating four-peptide pool. Th1 and Th2 cytokine production in response to the KRAS peptide pool is shown in FIG. 5. The most abundant individual cytokine detected in response to the KRAS peptide pool was IFN-γ, IL-2, and IL-17A, increasing ~7-, 5-, and 15-fold from baseline in splenocytes, respectively. Th2 cytokine production from the splenocytes in the vaccinated animals as compared to the adjuvant control did not increase notably. These data suggest that the immune responses of Th1 and Th17, but not Th2, were predominantly elicited by the current KRAS-specific peptide vaccine.

Discussion

In previous preclinical and clinical studies, KRAS mutant-specific CD4 and/or CD8 directed peptide epitopes have been identified. For example, a 9-mer peptide (4-12) covering the G12V mutation was shown to activate both CD4+ and CD8+ T cell responses in mice [15, 16]. A 17-mer peptide (5-21) was reported to induce CD4+ and CD8+ cytotoxic T lymphocytes immune responses specific for nested epitopes in one patient[14]. Vaccination with mutant RAS specific peptide or antigen-presenting cells (APCs) loaded with a mutated RAS peptide both generated mutant RAS specific T cell immune response [9, 17, 18]. The 17-mer KRAS peptide-pulsed APC vaccine induced cytotoxic T lymphocytes and cytokine responses specific to a given KRAS mutation in 26~42% of patients with several types of cancers, including lung cancer [19, 20]. In a phase II clinical trial, a 13-mer mutant RAS peptide vaccination showed a positive immune response, and potential but not statistically significant better disease-free survival and overall survival in pancreatic patients [10]. Many of these previous studies evaluated short peptide-based KRAS vaccines, overwhelmingly in patients with late-stage cancers. Thus, while much can be learned on the safety profiles and immunogenic activity of various KRAS peptides, their anti-tumor efficacy could not be definitively established.

Because constitutively active KRAS expression could induce immune suppressive environment in developing tumors, which may hamper the assessment of the preventive efficacy of the KRAS vaccine, we started the vaccination before KRAS activation in an inducible CCSP-KRAS murine model, where the vaccination was given before cancer development and thus, theoretically, in the absence of tumor-associated immunosuppression. In contrast to the majority of studies that employed short MHCI restricted peptide vaccines against KRAS, where CD8 cytotoxic T lymphocytes were the major focus, we used a different approach. We employed multiple and longer (15-20 amino acid) peptides, which were predicted to have optimal binding affinity to multiple MHC class II alleles. Mutant KRAS has been reported to be presented as both an MHC class I and class II epitope as a foreign antigen; we designed KRAS-derived peptides from hotspots of binding to MHC II in the murine system. Two of the four peptides used in our current KRAS vaccine were derived from outside of the mutation site in codon 12, while the remaining two 17-mer peptides were derived from the region containing either the wild-type or mutated peptide residue at position 12, with a thought to optimize sensitivity to the vaccine.

Several important findings were obtained from the current study. First, the vaccine was strikingly effective in preventing tumor development, causing a roughly 80% decrease in tumor volume in this highly aggressive model. Second, we showed that we could get a relatively strong immune response to these 15-20 length peptides using a combination of computer prediction and testing in mice. The observed immunologic response to the KRAS vaccine does not appear to be exclusive to the mutant peptide but rather to the entire wild-type peptides used. Third, because a substantial level of homology exists between the human and mouse KRAS protein, we were able to identify 15-17 amino acid peptides with 100% sequence identity between human and mouse within the hotspot regions, making it possible that these peptides could be translated directly into clinical studies. Fourth, the KRAS peptides employed in our study elicited predominantly Th1 and Th17 T cell responses, without eliciting a strong Th2 response. This suggests that protective immunity against KRAS-driven malignancy may primarily constitute Th1 and Th17 immune responses. Fifth, the draining lymph nodes of vaccinated animals had a substantial increase in the CD4+ T cell population, but not in the regulatory T cell population. This may have helped potentiate immune responses to the KRAS peptides.

One criticism of peptide vaccines compared with other strategies is a lack of antigen diversity. The induction of epitope spreading may be critical for the success of a peptide vaccine strategy [21]. In our study, we examined the presence of intra- and inter-antigen epitope spreading using an IFN-γ ELISPOT assay. Our preliminary data suggest that a limited intra-antigen epitope is spreading, as evidenced by strong INF-γ-secreting T cell responses to non-immunogen KRAS peptide in the vaccinated mice. It is possible that our vaccination strategy may have provoked an immune response to other areas of the KRAS protein, indicating the need for further studies to determine if the current multi-peptide KRAS vaccination is effective in stimulating natural processing and to demonstrate the presentation of the KRAS antigen in vivo.

In summary, we have shown that our KRAS-peptide-based vaccine targeting not only mutant KRASG12D but other wild-type regions induced robust Th1 and Th17 immune responses, which were associated with more than 80% inhibition of the KRAS-driven lung tumorigenesis. Our preclinical data warrant future studies to evaluate the efficacy of the vaccination against early lesions or in the setting of recurrence. Results obtained from such studies will have significant clinical relevance given that KRAS is the gene most frequently mutated across many cancer types.

Supplementary Material & Methods

Mice

Inducible TetOKRAS mice expressing murine KRAS with G12D mutation on FVB background were obtained from the NCI Mouse Models Consortium, and were then crossed with mice expressing the Tet-on Clara Cell Secreted Protein (CCSP) on the A/J background to permit tissue specific inducible expression of the transgene. For all experiments reported herein, only the F1 generation that harbor both KRASG12D and CCSP were used. All mice were housed in the Biomedical Resource Center at the Medical College of Wisconsin, Milwaukee, WI. All procedures were approved by the institutional animal care and use committee (IACUC).

Scoring System for the Prediction of MHC Class H Binding Epitopes

We and others have shown that peptides that score highly across multiple algorithms are most likely to yield strong immune responses. Therefore, we used the same multi-scoring system as previously described [18]. Briefly, to identify KRAS-specific MHC class II epitopes that have optimal binding affinity and promiscuity across multiple alleles, the following algorithms were used for prediction: SYFPEITHI (Institute for Cell Biology, Heidelberg, Germany), IEDB, and Rankpep (Harvard, Boston, MA).

The 11 peptides described in this study were selected as follows. For each available MHC Class II allele from the 3 algorithms, 20 peptide sequences were initially selected solely on the basis of the rank order of the predicted binding affinity. The sequences are approximately 15 amino acids in length. Individual amino acids for each selected peptide were assigned a score, with 1 being an amino acid contained in a peptide sequence that ranked highest for predictive binding affinity across multiple algorithms. Scoring individual amino acids accounted for the multiple peptides overlaps occurring within and across algorithms. The scores (S) for each amino acid were summed up across the multiple MHC Class II alleles from all 3 algorithms. Then, the number (N) of MHC class II alleles, for which each amino acid was predicted to have high affinity binding, was counted. The final score for each amino acid was calculated by multiplying S and N. For ease of identifying the most potentially immunogenic segments of the KRAS protein, each amino acid was assigned a color (from dark red to light blue) based on its final score percentile, with dark red being highest at ≥75% and light blue the lowest at <10% (FIG. 1A). Thus, the dark red color corresponds to a sequence where multiple peptides scored highly within an algorithm as well as across algorithms. Light blue represents sequences that are the least potentially immunogenic of all predicted high binding peptides. KRAS peptides were synthesized by Genemed Synthesis Inc. (South San Francisco, CA), purified by high-performance liquid chromatography, and characterized by mass spectrometry for use in all experiments.

Vaccine Preparation and Immunization

Mice were vaccinated with 50 μg of each peptide. Phosphate buffered saline (PBS) was added to bring the total volume to 50 μL/mouse. An equal amount of adjuvant (Complete Freund's Adjuvant or Incomplete Freund's Adjuvant) was added to bring the total volume to 100 μL/mouse. Mice were injected subcutaneously on the shoulder at 7 weeks of age, and boosting vaccination was given every two weeks for the first three boosting, and every 4 weeks for the last three boosting as shown in FIG. 2A. Transgene Kras was initiated with Dox diet (625 mg/kg diet) one week after the fourth vaccination, and Dox diet was given throughout of the study.

ELISPOT Assay

Cell suspensions from whole spleens were filtered through a 70 μm cell strainer (BD) and subjected to red blood cell lysis using ACK lysis buffer. $1.5 \sim 3.0 \times 10^4$ cells were plated into individual wells of a MAIPS4510 Multi-screen 96 well plate previously coated with anti-interferon γ detection antibody and containing media with either peptide, positive control (concanavalin A) or negative control (HIV peptide, or no antigen). After 72 hours, plates were washed and a secondary antibody (BD) was added and incubated on the plate overnight at 4 degrees Celsius. Wells were then washed with PBS and HRP streptavidin was added. Following 1 h incubation, the plate was developed using AEC substrate for between 5-25 minutes. The plate was subsequently gently washed under cold running tap water. When dry, an automated plate reader system (CTL Technologies) was used to image the plates and quantify spot number.

Magnetic Resonance Imaging

Mice were imaged using a 9.4T MRI (Bruker, Billerica, MA) with a custom birdcage style quadrature coil (Doty Scientific, Columbia, SC). Mice were anesthetized with isoflurane for the duration of the imaging procedure. Mice were induced at 2.5% isoflurane and maintained at 1.0-1.5%. Mouse heart rate, body temperature and respiratory rate were continuously monitored throughout imaging. Both respiratory and cardiac gating using an electrocardiogram were used to ensure that images were consistently acquired during latent periods of the respiratory cycle and at a consistent point during the cardiac cycle. Tumors were imaged using a multi-slice, multi-echo acquisition (MSME). Images were acquired using the following parameters; TE=8.07 ms, TR≥400 ms (variable), matrix=128×128, 1 average, 20 axial slices.

Lung Tumor Counting Using H&E Staining

Mouse lung samples from CCSP-KRASG12D mice were inflated and formalin fixed and processed (Sakura Tissue Tek VIPS) for paraffin embedding. After paraffin embedding, samples were sectioned at 4 μm (Microm HMS355S) onto poly-1-lysine coated slides and air dried at 45° C. overnight prior to immunohistochemistry or H&E staining.

H&E stained slides were scanned using the NanoZoomer slide scanner (Hamamatsu). Subsequently, NanoZoomer software was used and tumor regions were specifically highlighted and measured. Three slides were selected per mouse for analysis, corresponding to a ventral, midline and dorsal region of the lung.

Flow Cytometry

Mesenchymal lymph nodes, mouse lung or spleen were minced and processed to single cell suspensions. Single cells were evaluated using flow cytometry for expression of surface markers CD4, CD8, CD44, CD62L and CD25 (eBioscience), as well as intracellular staining for FoxP3 (eBioscience). Stained cells were fixed in 1% paraformaldehyde and were permeabilized following the manufacturer's instructions to evaluate the expression of intracellular targets (FoxP3). Flow cytometry was conducted using an LSR-II flow cytometer (BD). Data was analyzed using FlowJo software (Tree Star).

Cytokine Analysis

Mouse Th1/Th2/Th17 Cytokines Multi-AnalyteELISArray™ Kits (Qiagen) were used for cytokine analysis; it analyzes a panel of 12 cytokines involved in T helper cell biology. The cytokines represented by this array are IL2, IL4, IL5, IL6, IL10, IL12, IL13, IL17A, IL23, IFNγ, TNFα, and TGFβ1. Splenocytes from different groups of mice were stimulated with different peptides for 72 h, and then supernatant was collected and assayed based on the manufacturer's instructions.

Evaluation of Tumor-Infiltrating T Cells le;.4qTumors were frozen in Tissue-Tek OCT and stored at −80 C. Frozen tumors were then sectioned (8 mm), fixed in 75%/25% acetone/methanol for 5 minutes, and washed using PBS. Slides were incubated with normal goat serum (10% in PBS) for 1 hour at room temperature, washed, and incubated with rat anti-mouse CD8 (AbDSerotec) at 1:100 dilution in 10% goat serum/PBS overnight at 4 C. After washing, Alexa Fluor 488 goat anti-rat secondary antibody (Invitrogen) was added to the slides (1:1000) for one hour at room temperature. Prolong Gold antifade with 4', 6-diamidino-2-phenylindole (DAPI) mounting media (Invitrogen) was added after an additional wash and cover slips were attached. Positive cells and DAPI stained nuclei were counted in three random high-powered microscopic fields per slide and expressed as a mean. The number of positive cells in the field was expressed as # of CD8+ cells per mm$^2$ tumor area. Data are shown as the mean and SEM for 3 mice/group.

TABLE 2

Homology and sequence of peptides derived from Ki-Ras protein

| Kras peptides | Peptide sequence | % Homology with human Kras |
|---|---|---|
| G12D p5-21 G12D | KLVVVGADGVGKSALTI (SEQ ID NO: 2) | 100 |
| 61 p5-21 | KLVVVGAGGVGKSALTI (SEQ ID NO: 1) | 100 |
| 62 p5-19 | KLVVVGAGGVGKSAL (SEQ ID NO: 25) | 100 |
| 63 p17-31 | SALTIQLIQNHFVDE (SEQ ID NO: 4) | 100 |
| 64 p11-25 | AGGVGKSALTIQLIQ (SEQ ID NO: 26) | 100 |
| 65 p33-47 | DPTIEDSYRKQVVID (SEQ ID NO: 27) | 100 |
| 66 p40-54 | YRKQVVIDGETCLLD (SEQ ID NO: 28) | 100 |
| 67 p75-89 | GEGFLCVFAINNTKS (SEQ ID NO: 29) | 100 |
| 68 p78-92 | FLCVFAINNTKSFED (SEQ ID NO: 6) | 100 |
| 69 p130-144 | AQELARSYGIPFIET (SEQ ID NO: 30) | 93.9 |
| 70 p135-149 | RSYGIPFIETSAKTR (SEQ ID NO: 31) | 100 |
| 71 p154-168 | DAFYTLVREIRKHKE (SEQ ID NO: 32) | 73.3 |
| 72 p156-170 | FYTLVREIRKHKEKM (SEQ ID NO: 8) | 66.7 |

Example 2: Further Characterization of the K-Ras Vaccine

K-ras is the most frequently mutated member in human tumors, including adenocarcinomas of the pancreas (70~90% incidence), colon (~50%) and lung (25~50%). Germline K-RAS mutations were shown recently to be associated with multiple developmental disorders, including Noonan syndrome (NS), cardio-facio-cutaneous syndrome (CFCS), and Costello syndrome (CS). Specifically, K-RAS mutations at amino acid positions K5, V14, Q22, P34, I36, T58, G60, V152, D153, and F156 is remarkably broad and comprises NS, CFC. No specific therapies targeting K-ras have been developed, partially due to the lack of druggable pockets and cavities on the RAS surface; the development of alternative therapies or preventive measures has great appeal.

In the above-example, the inventors have shown that the newly developed K-ras multi-peptide vaccine is highly effective in primary immunoprevention of lung cancer development in a conditional K-ras-driven lung cancer model, where vaccination was given before oncogenic K-ras expression started. To further the application of K-ras vaccine in secondary or tetherary preventing, which is more relevant clinically, as in high risk population, individual has already been exposed to environmental carcinogens or already carries K-ras mutations or amplifications. The inventors tested K-ras vaccine in carcinogen induced K-ras-driven model and in a genetic model, where K-ras mutation started way before vaccination. The Kras-vaccine used in this Example comprises the four (4) peptides found in Table 1, specifically SEQ ID NO:1, SEQ ID NO:2, SEQ ID NO:4 and SEQ ID NO:6, and is referred to as the "K-ras multi-peptide vaccine" or "K-ras vaccine" herein. Since the multi-peptide vaccination mostly boosts T cell immunity to function, we further investigated ways that can synergize with K-ras vaccine, such as combination with agents that facilitate T cell infiltration, or with immune checkpoint inhibitors to block immune suppressive environment.

K-Ras Vaccine is Effective and Shows Synergistic Effect with UAB30, an Analog of Retinoid X Receptor (RXR) Agonist Bexarotene, in Inhibiting Tumorigenesis in K-rasLA1 Model.

Figure 7:
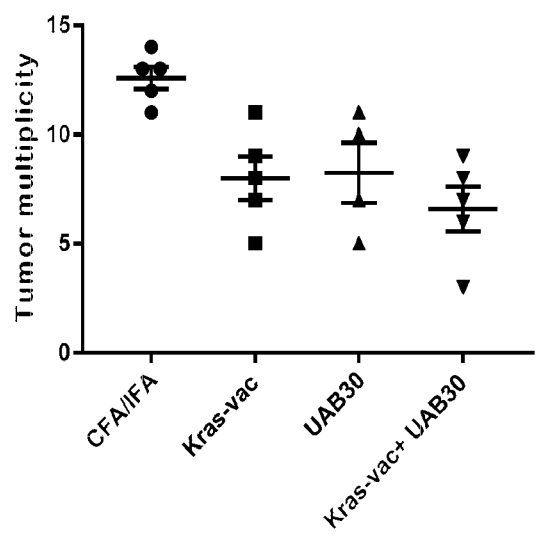
FIG. 7. K-ras vaccine synergizes with UAB30 in K-rasLA1 model. Kras-vaccination was given to K-rasLA1 mice at 8~10 weeks old at which numerous pleural lesions already formed in lung. Mice were also treated with UAB30 alone, or the combination of UAB30 and K-ras vaccine. Tumor multiplicity and tumor load were determined.
Figure 7:
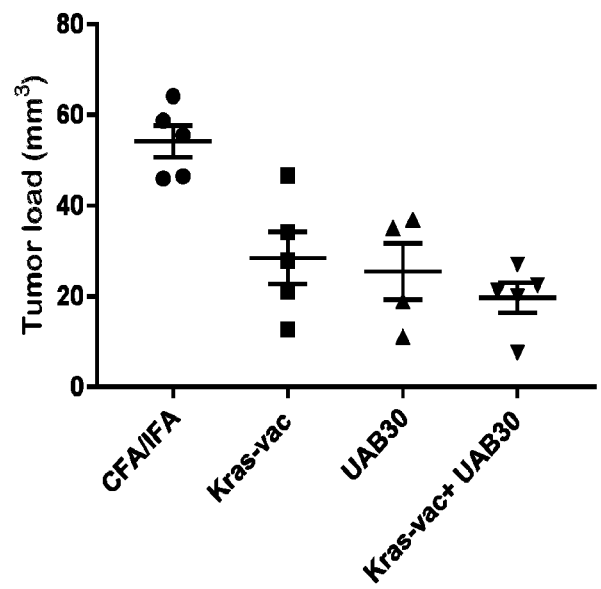
Figure 8:
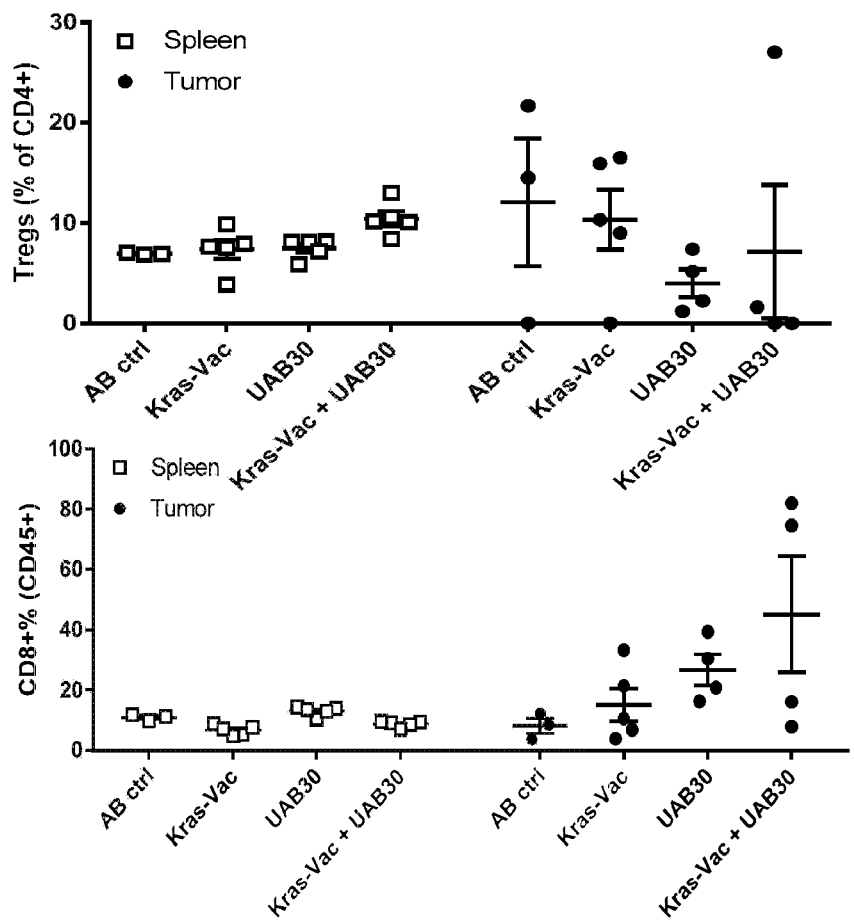
FIG. 8. UAB30 increased tumor infiltrated CD8+ cells and decreased Tregs in tumor. K-rasLA1 mice were treated with control, Kras-vaccine, UAB30 alone or Kras-vaccine and UAB30 and the % CD4+ or CD8+ T cells were assessed in the spleen or tumor of mice at 4~5 weeks after treatment.

K-rasLA1 mouse develops premalignant lung lesions that progress to multifocal lung adenocarcinomas due to somatic mutations in K-ras, which occurs at the birth of these mice through DNA recombination. The spontaneous nature of K-ras activation in this model closely recapitulates spontaneous oncogene activation as seen in human cancers, therefore represents as a more clinically relevant K-ras-drive lung tumor model. In this model, vaccination was given when mice were 8~10 weeks old, at which numerous pleural lesions already formed in lung, yet K-ras vaccination alone significant inhibited lung tumor multiplicity and load in K-rasLA1 mice, decreased tumor numbers from ~12 to ~7 per mouse, and tumor load from ~55 mm$^3$ to ~30 mm$^3$ (FIG. 7). UAB30 is a low-toxicity RXR agonist, which significantly increased infiltrated CD8+ cells and decreased Tregs in tumors (FIG. 8), and when combined with K-ras vaccination, induced better anti-tumor efficacy (FIG. 7).

K-Ras Vaccine Inhibits Carcinogen MNU-Induced Lung Tumorigenesis

N-Nitroso-N-methylurea (MNU) is an alkylating agent, and exhibits its toxicity by transferring its methyl group to nucleobases in nucleic acids, which can lead to AT: GC transition mutations, specifically it induces massive K-ras mutations, therefore, is a highly reliable carcinogen, mutagen, and teratogen, has been reported to induce cancers in multiple organ sited in a wide range of experimental animals. Formation of MNU upon nitrosation in various food samples, such as Smoked/Dried Fish, Fish Sauce, Seafoods, and Ethnic Fermented/Pickled Vegetables, have been reported, posted as relevant carcinogen induction model to mimic human cancer development.

Figure 9:
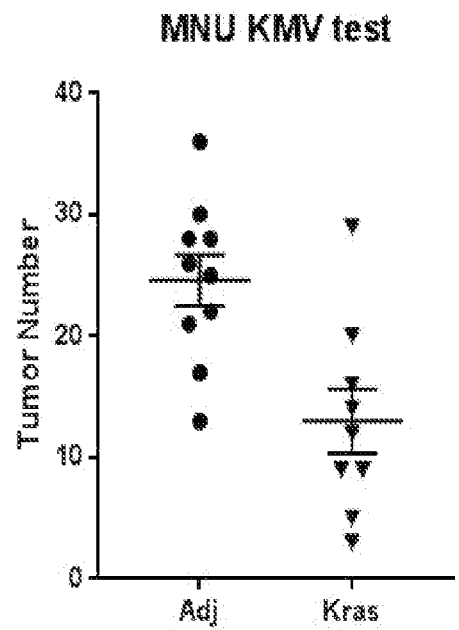
FIG. 9. K-ras vaccine inhibit both tumor number and tumor load in MNU-induced mouse lung adenoma model. MNU-model mice were treated with adjuvant or Kras vaccine 4 weeks post MNU induction, and the number of tumors and tumor load was assayed at week 19 after treatment started.
Figure 9:
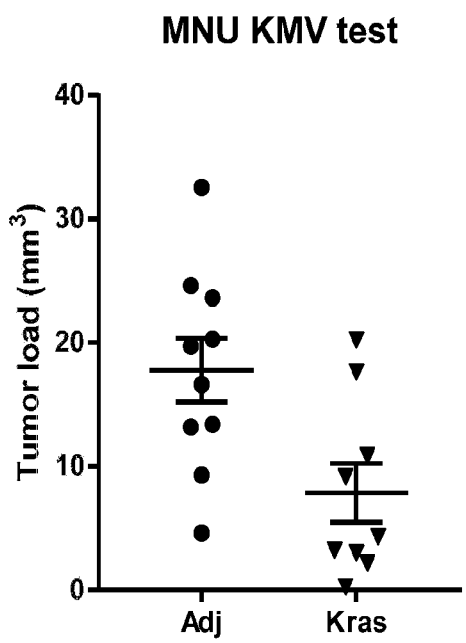

In this model, K-ras vaccination was given 4 weeks post NMU induction, as shown in FIG. 9, vaccination alone reduced tumor number from ~25 to ~12, and decreased tumor load from ~18 mm$^3$ to ~9 mm$^3$, caused an overall ~50% inhibition on tumor formation, suggesting it can prevent tumorigenesis in post-initiation setting, could be benefit to high risk populations that already exposed to K-ras mutation.

K-Ras Vaccine Synergizes with Avasamibe in K-Ras-Driven Lung Cancer Syngraft Tumor Model.

Cholesterol, especially aberrant accumulation of cholesteryl ester, is a critical component of the plasma membrane, has been recently implicated to promote cancer cell growth and metastasis. Avasimibe, a specific inhibitor for the key enzyme ACAT1 that mediating cholesteryl esterification, has recently been shown to promote anti-tumor immune responses by targeting tumor-specific CD8+ cytotoxic T cells. Avasimibe inhibits cholesterol esterification; upregulates plasma membrane cholesterol levels, enhances TCR clustering, and promotes formation of the immunological synapse in CD8+ T cells, which is essential for promoting T cell mediated anti-tumor immunity.

Figure 10:
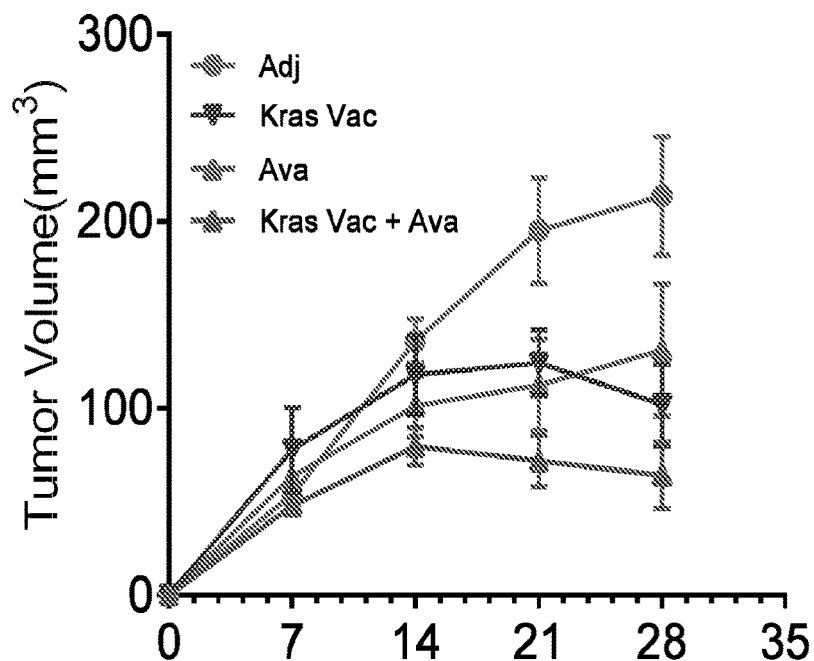
FIG. 10. K-ras vaccine synergize with Avasamibe to inhibit lung tumor progression in K-ras-driven lung cancer syngraft tumor model.

Therefore, we tested the combination of K-ras multi-peptide vaccine with avasimibe in a K-ras-driven lung cancer syngraft model. The results show that both avasimibe and K-ras vaccination are effective in inhibiting tumor growth, and an additive effect was achieved with combined treatment (FIG. 10).

K-Ras Vaccine Synergizes with Anti-Vista in K-Ras-Driven Pancreatic Cancer Syngraft Tumor Model.

Immune checkpoint proteins CTLA-4, PD-1 and VISTA suppress anti-tumor immune responses, specifically impeding T cell activity against cancer, therefore combining immune checkpoint inhibitors with vaccine is predicted to offer synergistic anti-tumor efficacy, currently, multiple clinical trials are ongoing testing multi-peptide vaccine combination with anti-PD1 or anti-CTLA-4. Here we examined the efficacy of blocking VISTA combined with K-RAS vaccine in preventing K-ras-driven pancreatic cancer progression in a syngraft tumor model. Our results show that both anti-VISTA and K-ras vaccination are effective in inhibiting tumor growth, and an additive effect was achieved with combined treatment (FIG. 11).

K-ras vaccine is also being tested with PD-1 and PD-LI peptide vaccine described in more detail below. Briefly, peptides p13, p76, and p228 against PD-L1 and p21, p94, p193 and p228 were tested in combination with the KRAS vaccine (KRAS vaccine comprising four peptides SEQ ID NO:1, SEQ ID NO:2, SEQ ID NO:4 and SEQ ID NO:6 it Table 1). Results are expected to show similar results as with anti-VISTA, specifically the combination shows the ability to inhibit tumor growth.

Example 3: Develop New Peptide Vaccine Against Immune Checkpoint PD-1 and PD-L1

Cancer cells are naturally attacked by cells of the immune system, but can induce a state of tolerance whereby they escape from immune attack, for which immune checkpoint proteins such as PD1, VISTA are important ones mediating this immune escape. Interaction of PD-1 on activated T cells and PD-L1 on cancer cells lead to inhibition of the cytotoxic T cells. Investigators have recently identified spontaneous T cell reactivity against PD-L1 in the tumor microenvironment and in the peripheral blood of patients with metastatic melanoma and healthy donors, PD-L1 reactive CD8 T cells are cytotoxic and can kill cancer cells and immune regulatory cells in vitro, and responsive PD-L1 peptide vaccine has therefore under development. Here, by using a multi-scoring system that combines multiple MHC class II peptide binding algorithms, we identified immunogenic "hotspots", and selected 7 peptides for PD-L1 and 11 peptides for PD-1 from these immunogenic "hot" regions (see Table 3). We then tested their immunogenicity in naïve mice using the IFN-γ ELISPOT assay. Of the 7 designed peptides, three of them were immunogenic, with p13, p76, and p228 against PD-L1 eliciting the strongest IFN-γ response (FIG. 12 upper panel), and p21, p94, p193 and p228 for PD-1 eliciting the strongest IFN-γ response (FIG. 12 lower panel). As expected, mice immunized with adjuvant alone did not develop any antigen-specific IFN-γ response to either single peptide or multipeptide stimulation, with the mean IFN-γ response similar to that of the HIV peptide (P<0.0001, data not shown).

TABLE 3

Homology and sequence designed for PD-1 and PD-L1

| Pep Name | Mouse seq | | homology |
|---|---|---|---|
| mPD1 - 21 | SWQSGWLLEVPNGPW | (SEQ ID NO: 33) | 46.7% |
| mPD1 - 94 | QDARFQIIQLPNRHD | (SEQ ID NO: 34) | 67% |
| mPD1 - 117 | RRNDSGIYLCGAISL | (SEQ ID NO: 35) | 93% |
| mPD1 - 193 | LAVFCSTSMSEARGA | (SEQ ID NO: 36) | 46.7% |
| mPD1 - 205 | GSKDDTLKEEPSAAP | (SEQ ID NO: 37) | 46.7% |
| mPD1 - 216 | KEEPSAAPVPSVAYE | (SEQ ID NO: 38) | 67% |
| mPDL1-13 | CHLLRAFTITAPKDL | (SEQ ID NO: 39) | 73% |
| mPDL1-76 | PQHSNFRGRASLPKD | (SEQ ID NO: 40) | 60% |
| mPDL1228 | LPATHPPQNRTHWVL | (SEQ ID NO: 41) | 60% |

Table 4 shows potential immunogenic peptide sequences designed for human use.

TABLE 4

Potential immunogenic peptide Sequence designed for human PD-1 and human PD-L1

| Pep Name | Human seq | |
|---|---|---|
| hPD1 - 21 | GWRPGWFLDSPDRPW | (SEQ ID NO: 42) |
| hPD1-61 | ESFVLNWYRMSPSNQTDKL | (SEQ ID NO: 43) |
| hPD1 - 94 | QDCRFRVTQLPNGRD | (SEQ ID NO: 44) |
| hPD1 - 117 | RRNDSGTYLCGAISL | (SEQ ID NO: 45) |
| hPD1 - 193 | LAVICSRAARGTIGA | (SEQ ID NO: 46) |
| hPD1-193L | LAVICSRAARGTIGARRTG | (SEQ ID NO: 47) |
| hPD1 - 205 | RRTGQPLKEDPSAVP | (SEQ ID NO: 48) |
| hPD1 - 216 | KEDPSAVPVFSVDYG | (SEQ ID NO: 49) |

TABLE 4-continued

Potential immunogenic peptide Sequence designed for human PD-1 and human PD-L1

| Pep Name | Human seq | |
|---|---|---|
| hPDL1-13 | WHLLNAFTVTVPKDL | (SEQ ID NO: 50) |
| hPDL1-76 | VQHSSYRQRARLLKD | (SEQ ID NO: 51) |
| hPDL1-112 | YRCMISYGGADYKRI | (SEQ ID NO: 52) |
| hPDL1-228 | LPLAHPPNERTHLVI | (SEQ ID NO: 53) |
| hPDL1-255 | LTFIFRLRKGRMMDV | (SEQ ID NO: 54) |

PD-1/PD-L1 Peptide Vaccine Exhibit Excellent Anti-Tumor Activity in Syngraft Tumor Model Further testing anti-tumor efficacy of these newly developed PD-1/PD-L1 peptide in a K-ras-Driven tumor model, we found that compare to antibodies, multi-peptide vaccines demonstrate an equal or even better anti-cancer efficacy, suggesting it could be beneficial clinically (FIG. 13).

Example 4: A Phase I Study with a Novel Cancer Vaccine (KRAS/PD-1/PD-L1) in Patients with Pancreatic, Lung, or Colon Cancer This example evaluates the combination of KRAS vaccine described herein in combination with PD-1/PDL1 vaccine in pancreatic, lung and colon cancer. Information will be collected about the specific characteristics of the participant's own KRAS mutation status. It is known that pancreatic, lung, and colon cancers have KRAS mutations that are specific to an individual patient's tumor and the resulting mutant KRAS proteins are neo-antigens. Mutant KRAS proteins can be used as vaccines to induce strong immune responses, which may help the participant's body to fight residual tumor cells (minimal residual disease situation) that could cause the recurrence or metastasis in the future. The goal of study will be to examine the safety of the vaccine when given at several different time points and will examine the vaccine induced an immune response. The study aims to enroll 28 participants.
  Experimental: KRAS/PD-1/PD-L1 Vaccine (peptides+poly-ICLC)
  Poly-ICLC: 4×0.5 mg (total dose 2 mg) given on days 1, 4, 8, 15, 22, 78, and 162
  Peptides: 4×300 mcg per peptide given on days 1, 4, 8, 15, 22, 78, and 162
  Biological: Poly-ICLC
  Biological: KRAS, PD-1 and PD-L1 Peptides
  The participants will be monitored and assayed for the following primary outcomes: (a) number of participants experiencing clinical and laboratory adverse events (AEs) [Time Frame: 7 weeks from first study drug administration], and (b) number of participants for KRAS mutation status assessment [Time Frame: 12 weeks].
  The participants will also be monitored for the following secondary outcomes: (a) number of participants with specific cellular immune responses following administration of the vaccine [Time Frame: 16 weeks], and (b) number of participants alive without progression at two years after surgery following administration of the vaccine [Time Frame: 2 Years].
  Participants will be selected that are 18 year or older and meeting the following criteria on screening examination to be eligible to participate in the study:

Patients with resectable and borderline resectable cancer who have (a) completed all planned curative intent therapy, (b) no clinical and radiographic evidence of recurrent or metastatic disease, (c) no contraindications to peptide vaccine therapy, and (d) consented to trial participation will be eligible for the study.

This pre-surgery baseline assessment must be documented by complete physical examination and imaging studies. Imaging studies must include a total body PET-CT.

Women of childbearing potential must have a negative pregnancy test before entry onto the trial and within 7 days prior to start of study medication, because of the unknown effects vaccine on the developing human fetus.

Female and male patients must agree to use effective contraception.

Exclusion Criteria:

Prior treatment with immune-modulatory agents including, but not limited to: PD-1/PD-L1 blockade, CTLA-4 blockade, IL-2, CD40 stimulation, CD137 stimulation Prior investigational cancer-directed cancer vaccine therapy, bone marrow or stem cell transplant, targeted therapy, other investigational anti-cancer therapies, immunosuppressive agents, chronic use of systemic corticosteroids, or vaccine therapy for prevention of infectious diseases History of severe allergic reactions attributed to any vaccine therapy for the prevention of infectious diseases or any other non-oncology diseases Know autoimmune disease or immunosuppressive conditions with the exception of vitiligo, type 1 diabetes, residual autoimmune-related hypothyroidism, psoriasis, or chronic infections with HIV, hepatitis B or C Active infection, symptomatic congestive heart failure, unstable angina pectoris, cardiac arrhythmia Pregnant women or nursing women are excluded from this study because the vaccine and poly-ICLC are agents with unknown risks We expect that the vaccine will provide improved treatment of the cancer and an increase in survival rate and an increase in time or reduction in reoccurrence of the cancer.

Each publication, patent, and patent publication cited in this disclosure is incorporated in reference herein in its entirety. The present invention is not intended to be limited to the foregoing examples, but encompasses all such modifications and variations as come within the scope of the appended claims.

---

We claim:

1. A vaccine composition comprising (1) (i) at least four peptides of KRAS, wherein the peptides of KRAS are selected from the group consisting of SEQ ID Nos. 1, 2, 3, 4, 5, 6, 7, 8, 9, 10, 11, 12, wherein one of the peptides of KRAS is selected from the group consisting of SEQ ID NO: 7, 8, 9, 10, 11, 12 or (ii) one or more vectors comprising a nucleic acid sequence encoding four KRAS peptides consisting of SEQ ID Nos. 1, 2, 3, 4, 5, 6, 7, 8, 9, 10, 11, 12, wherein one of the encoded peptides of KRAS is selected from the group consisting of SEQ ID NO: 7, 8, 9, 10, 11, 12 and (2) an adjuvant, wherein the vaccine composition elicits an anti-tumor immune response in a subject.

2. The vaccine composition of claim 1, wherein the vaccine composition comprises four KRAS peptides, wherein the four KRAS peptides consist of the amino acid sequence of SEQ ID NO: 1 (P5-21WT: KLVVVGAGGVGKSALTI), 4 (P17: SALTIQLIQNHFVDE), 6 (P78: FLCVFAINNTKSFED) and 8 (P156: FYTLVREIRKHKEKM).

3. The vaccine composition of claim 1, wherein the adjuvant is selected from the group consisting of GM-CSF, cyclic dinucleotide (CDN), Aluminum, monophosphoryl lipid A (MPL), and STING ligands.

4. The vaccine composition of claim 1, wherein the vaccine composition further comprises a pharmaceutically acceptable carrier.

5. A vector comprising an isolated nucleic acid sequence encoding the KRAS peptides of claim 1 operatively linked to a heterologous transcriptional regulatory element.

6. A method of eliciting an anti-tumor immune response in a subject in need thereof, the method comprising:
administering an effective amount a vaccine composition of claim 1 to the subject, wherein the vaccine composition elicits an anti-tumor immune response.

7. The method of claim 6, wherein the anti-tumor immune response reduces the number of tumor cells in a subject or tumor size in the subject.

8. The method of claim 6, wherein the method further comprises:
administering to the subject at least one checkpoint inhibitor.

9. The method of claim 8, wherein the checkpoint inhibitor is administered co-currently with the vaccine composition.

10. The method of claim 8, wherein the checkpoint inhibitor is selected from the group consisting of anti-PD-L1 antibody, anti-VISTA antibody, TIM3 antibody, CTLA-4 antibody, PD-1 peptide, PD-L1 peptide, small molecule PD-1 inhibitor, and a combination thereof.

11. The method of claim 10, wherein the checkpoint inhibitor is at least one PD-1 peptide, at least one PD-L1 peptide, at least one small molecule PD-1 inhibitor, or a combination thereof.

12. The method of claim 6, wherein the method further comprises administering at least one NSAIDs to the subject.

13. The method of claim 6, wherein the method further comprises administering a RXR agonist, wherein the RXR agonist is selected from the group consisting of bexarotene, UAB30, and low dose retinoic acid.

14. The method of claim 6, wherein the method further comprises administering avasimibe in combination with the Kras-vaccine in an effective amount to elicit an antitumor response.

15. The method of claim 6, wherein the subject is a human suffering from a cancer that contains a KRAS mutation.

16. The method of claim 6, wherein the subject is a human with lung cancer, pancreatic cancer, or colon cancer.

17. The method of claim 6, wherein the method further comprises treating the subject with irradiation or chemotherapy.

18. A method to reduce or slow the progression or development of cancer in a patient at risk of developing a KRAS-associated cancer, the method comprising:
   determining if a patient is at risk of developing a KRAS associated cancer; and
   treating the patient with a vaccine composition of claim 1.

19. The method of claim 18, wherein the step of determining if a patient is at risk of developing a KRAS associated cancer comprises:
   detecting a mutation of KRAS in a sample from the patient.

20. The method of claim 18, wherein the treating step further comprises administering avasimibe with the vaccine in an effective amount to treat the cancer.

21. The method of claim 18, wherein the treating step further comprises administering a checkpoint inhibitor, the checkpoint inhibitor is selected from the group consisting of anti-PD-L1 antibody, anti-VISTA antibody, TIM3 antibody, CTLA-4 antibody, PD-1 peptide, PDL-1 peptide, small molecule PD-1 inhibitor, and a combination thereof, wherein the combination of the vaccine and checkpoint inhibitor in combination reduce or slow the progression or development of cancer.

22. The method of claim 18, wherein the method further comprises administering at least one RXR agonist, wherein the RXR agonist is selected from the group consisting of bexarotene, UAB30, and low dose retinoic acid.

\* \* \* \* \*

UNITED STATES PATENT AND TRADEMARK OFFICE
CERTIFICATE OF CORRECTION

PATENT NO. : 11,771,749 B2
APPLICATION NO. : 16/483332
DATED : October 3, 2023
INVENTOR(S) : Jing Pan et al.

It is certified that error appears in the above-identified patent and that said Letters Patent is hereby corrected as shown below:

In the Specification

Column 8, Line 44, "Nosi" should be --NOs:--.

Column 17, Line 13, "VIPS" should be --VIP5--.

Column 17, Line 15, "poly-1-lysine" should be --poly-l-lysine--.

Column 18, Line 5, "H" should be --II--.

Column 21, Line 60, "H" should be --II--.

Column 23, Line 16, "VIPS" should be --VIP5--.

Column 23, Line 18, "poly-1-lysine" should be --poly-l-lysine--.

Column 25, Line 11, "136" should be --I36--.

In the Claims

Column 50, Claim 21, Line 10, "PDL-1" should be --PD-L1--.

Signed and Sealed this
Ninth Day of January, 2024

Katherine Kelly Vidal
Director of the United States Patent and Trademark Office

SEQUENCE LISTING

```
<160> NUMBER OF SEQ ID NOS: 54

<210> SEQ ID NO 1
<211> LENGTH: 17
<212> TYPE: PRT
<213> ORGANISM: Artificial Sequence
<220> FEATURE:
<223> OTHER INFORMATION: Synthetic- p5-21WT KRAS peptide

<400> SEQUENCE: 1

Lys Leu Val Val Val Gly Ala Gly Gly Val Gly Lys Ser Ala Leu Thr
1               5                   10                  15

Ile

<210> SEQ ID NO 2
<211> LENGTH: 17
<212> TYPE: PRT
<213> ORGANISM: Artificial Sequence
<220> FEATURE:
<223> OTHER INFORMATION: Synthetic- p5-21G12D KRAS peptide

<400> SEQUENCE: 2

Lys Leu Val Val Val Gly Ala Asp Gly Val Gly Lys Ser Ala Leu Thr
1               5                   10                  15

Ile

<210> SEQ ID NO 3
<211> LENGTH: 17
<212> TYPE: PRT
<213> ORGANISM: Artificial Sequence
<220> FEATURE:
<223> OTHER INFORMATION: Synthetic p5-21G12V KRAS peptide

<400> SEQUENCE: 3

Lys Leu Val Val Val Gly Ala Val Gly Val Gly Lys Ser Ala Leu Thr
1               5                   10                  15

Ile

<210> SEQ ID NO 4
```

```
<211> LENGTH: 15
<212> TYPE: PRT
<213> ORGANISM: Artificial Sequence
<220> FEATURE:
<223> OTHER INFORMATION: Synthetic- p17 KRAS peptide

<400> SEQUENCE: 4

Ser Ala Leu Thr Ile Gln Leu Ile Gln Asn His Phe Val Asp Glu
1               5                   10                  15

<210> SEQ ID NO 5
<211> LENGTH: 18
<212> TYPE: PRT
<213> ORGANISM: Artificial Sequence
<220> FEATURE:
<223> OTHER INFORMATION: Synthetic- p16 KRAS peptide

<400> SEQUENCE: 5

Lys Ser Ala Leu Thr Ile Gln Leu Ile Gln Asn His Phe Val Asp Glu
1               5                   10                  15

Tyr Asp

<210> SEQ ID NO 6
<211> LENGTH: 15
<212> TYPE: PRT
<213> ORGANISM: Artificial Sequence
<220> FEATURE:
<223> OTHER INFORMATION: Synthetic- p78 KRAS peptide

<400> SEQUENCE: 6

Phe Leu Cys Val Phe Ala Ile Asn Asn Thr Lys Ser Phe Glu Asp
1               5                   10                  15

<210> SEQ ID NO 7
<211> LENGTH: 19
<212> TYPE: PRT
<213> ORGANISM: Artificial Sequence
<220> FEATURE:
<223> OTHER INFORMATION: Synthetic- p75 KRAS peptide

<400> SEQUENCE: 7

Thr Gly Glu Gly Phe Leu Cys Val Phe Ala Ile Asn Asn Thr Lys Ser
1               5                   10                  15

Phe Glu Asp

<210> SEQ ID NO 8
<211> LENGTH: 15
<212> TYPE: PRT
<213> ORGANISM: Artificial Sequence
<220> FEATURE:
<223> OTHER INFORMATION: Synthetic- p156 KRAS peptide

<400> SEQUENCE: 8

Phe Tyr Thr Leu Val Arg Glu Ile Arg Lys His Lys Glu Lys Met
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Synthetic- p156 human KRAS peptide

<400> SEQUENCE: 9

Phe Tyr Thr Leu Val Arg Glu Ile Arg Gln Tyr Arg Leu Lys Lys Ile
1               5                   10                  15
```

Ser

<210> SEQ ID NO 10
<211> LENGTH: 23
<212> TYPE: PRT
<213> ORGANISM: Artificial Sequence
<220> FEATURE:
<223> OTHER INFORMATION: Synthetic- p11 KRAS peptide

<400> SEQUENCE: 10

Ala Gly Gly Val Gly Lys Ser Ala Leu Thr Ile Gln Leu Leu Gln Asn
1               5                   10                  15

His Phe Val Asp Glu Tyr Asp
            20

<210> SEQ ID NO 11
<211> LENGTH: 21
<212> TYPE: PRT
<213> ORGANISM: Artificial Sequence
<220> FEATURE:
<223> OTHER INFORMATION: Synthetic- p11s KRAS peptide

<400> SEQUENCE: 11

Ala Gly Gly Val Gly Lys Ser Ala Leu Thr Ile Gln Leu Leu Gln Asn
1               5                   10                  15

His Phe Val Asp Glu
            20

<210> SEQ ID NO 12
<211> LENGTH: 25
<212> TYPE: PRT
<213> ORGANISM: Artificial Sequence
<220> FEATURE:
<223> OTHER INFORMATION: Synthetic- p9 KRAS peptide

<400> SEQUENCE: 12

Val Gly Ala Gly Gly Val Gly Lys Ser Ala Leu Thr Ile Gln Leu Leu
1               5                   10                  15

Gln Asn His Phe Val Asp Glu Tyr Asp
            20                  25

<210> SEQ ID NO 13
<211> LENGTH: 51
<212> TYPE: DNA
<213> ORGANISM: Artificial Sequence
<220> FEATURE:
<223> OTHER INFORMATION: Synthetic- p5-21 KRAS nucleotide

<400> SEQUENCE: 13
aagctggtgg tggtgggcgc cggcggcgtg ggcaagagcg ccctgaccat c          51

<210> SEQ ID NO 14
<211> LENGTH: 51
<212> TYPE: DNA
<213> ORGANISM: Artificial Sequence
<220> FEATURE:
<223> OTHER INFORMATION: Synthetic- p5-21G12D KRAS nucleotide

<400> SEQUENCE: 14
aagctggtgg tggtgggcgc cgacggcgtg ggcaagagcg ccctgaccat c          51

<210> SEQ ID NO 15
<211> LENGTH: 51
<212> TYPE: DNA

<213> ORGANISM: Artificial Sequence
<220> FEATURE:
<223> OTHER INFORMATION: Synthetic- p5-21G12V KRAS nucleotide

<400> SEQUENCE: 15
aagctggtgg tggtgggcgc cgtgggcgtg ggcaagagcg ccctgaccat c        51

<210> SEQ ID NO 16
<211> LENGTH: 45
<212> TYPE: DNA
<213> ORGANISM: Artificial Sequence
<220> FEATURE:
<223> OTHER INFORMATION: Synthetic- p17 KRAS nucleotide

<400> SEQUENCE: 16
agcgccctga ccatccagct gatccagaac cacttcgtgg acgag        45

<210> SEQ ID NO 17
<211> LENGTH: 54
<212> TYPE: DNA
<213> ORGANISM: Artificial Sequence
<220> FEATURE:
<223> OTHER INFORMATION: Synthetic- p16 KRAS nucleotide

<400> SEQUENCE: 17
aagagcgccc tgaccatcca gctgatccag aaccacttcg tggacgagta cgac        54

<210> SEQ ID NO 18
<211> LENGTH: 45
<212> TYPE: DNA
<213> ORGANISM: Artificial Sequence
<220> FEATURE:
<223> OTHER INFORMATION: Synthetic- p78 KRAS nucleotide

<400> SEQUENCE: 18
ttcctgtgcg tgttcgccat caacaacacc aagagcttcg aggac        45

<210> SEQ ID NO 19
<211> LENGTH: 57
<212> TYPE: DNA
<213> ORGANISM: Artificial Sequence
<220> FEATURE:
<223> OTHER INFORMATION: Synthetic- p75 KRAS nucleotide

<400> SEQUENCE: 19
accggcgagg gcttcctgtg cgtgttcgcc atcaacaaca ccaagagctt cgaggac        57

<210> SEQ ID NO 20
<211> LENGTH: 45
<212> TYPE: DNA
<213> ORGANISM: Artificial Sequence
<220> FEATURE:
<223> OTHER INFORMATION: Synthetic- p156 KRAS nucleotide

<400> SEQUENCE: 20
ttctacaccc tggtgaggga gatcaggaag cacaaggaga agatg        45

<210> SEQ ID NO 21
<211> LENGTH: 51
<212> TYPE: DNA
<213> ORGANISM: Artificial Sequence
<220> FEATURE:
<223> OTHER INFORMATION: Synthetic- p156 human KRAS nucleotide

<400> SEQUENCE: 21
ttctacaccc tggtgaggga gatcaggcag tacaggctga agaagatcag c        51

<210> SEQ ID NO 22
<211> LENGTH: 69
<212> TYPE: DNA
<213> ORGANISM: Artificial Sequence
<220> FEATURE:
<223> OTHER INFORMATION: Synthetic- p11 KRAS nucleotide

<400> SEQUENCE: 22
gccggcggcg tgggcaagag cgccctgacc atccagctgc tgcagaacca cttcgtggac    60
gagtacgac                                                            69

<210> SEQ ID NO 23
<211> LENGTH: 63
<212> TYPE: DNA
<213> ORGANISM: Artificial Sequence
<220> FEATURE:
<223> OTHER INFORMATION: Synthetic- p11s KRAS nucleotide

<400> SEQUENCE: 23
gccggcggcg tgggcaagag cgccctgacc atccagctgc tgcagaacca cttcgtggac    60
gag                                                                  63

<210> SEQ ID NO 24
<211> LENGTH: 75
<212> TYPE: DNA
<213> ORGANISM: Artificial Sequence
<220> FEATURE:
<223> OTHER INFORMATION: Synthetic- p9 KRAS nucleotide

<400> SEQUENCE: 24
gtgggcgccg gcggcgtggg caagagcgcc ctgaccatcc agctgctgca gaaccacttc    60
gtggacgagt acgac                                                     75

<210> SEQ ID NO 25
<211> LENGTH: 15
<212> TYPE: PRT
<213> ORGANISM: Artificial Sequence
<220> FEATURE:
<223> OTHER INFORMATION: Synthetic- p5-19 KRAS peptide

<400> SEQUENCE: 25

Lys Leu Val Val Val Gly Ala Gly Gly Val Gly Lys Ser Ala Leu
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic- p11-25 KRAS peptide

<400> SEQUENCE: 26

Ala Gly Gly Val Gly Lys Ser Ala Leu Thr Ile Gln Leu Ile Gln
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic- p33-47 KRAS peptide

<400> SEQUENCE: 27

Asp Pro Thr Ile Glu Asp Ser Tyr Arg Lys Gln Val Val Ile Asp
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic- p40-54 KRAS peptide

<400> SEQUENCE: 28

Tyr Arg Lys Gln Val Val Ile Asp Gly Glu Thr Cys Leu Leu Asp
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic- p75-89 KRAS peptide

<400> SEQUENCE: 29

Gly Glu Gly Phe Leu Cys Val Phe Ala Ile Asn Asn Thr Lys Ser
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic- p130-144 KRAS peptide

<400> SEQUENCE: 30

Ala Gln Glu Leu Ala Arg Ser Tyr Gly Ile Pro Phe Ile Glu Thr
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic- p135-149 KRAS peptide

<400> SEQUENCE: 31

Arg Ser Tyr Gly Ile Pro Phe Ile Glu Thr Ser Ala Lys Thr Arg
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic- p154-168 KRAS peptide

<400> SEQUENCE: 32

Asp Ala Phe Tyr Thr Leu Val Arg Glu Ile Arg Lys His Lys Glu
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic- mPD1-21 peptide

<400> SEQUENCE: 33

Ser Trp Gln Ser Gly Trp Leu Leu Glu Val Pro Asn Gly Pro Trp

<210> SEQ ID NO 34
<211> LENGTH: 15
<212> TYPE: PRT
<213> ORGANISM: Artificial Sequence
<220> FEATURE:
<223> OTHER INFORMATION: Synthetic- mPD1-94 peptide

<400> SEQUENCE: 34

Gln Asp Ala Arg Phe Gln Ile Ile Gln Leu Pro Asn Arg His Asp
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic- mPD1-117 peptide

<400> SEQUENCE: 35

Arg Arg Asn Asp Ser Gly Ile Tyr Leu Cys Gly Ala Ile Ser Leu
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic- mPD1-193 peptide

<400> SEQUENCE: 36

Leu Ala Val Phe Cys Ser Thr Ser Met Ser Glu Ala Arg Gly Ala
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic- mPD1-205 peptide

<400> SEQUENCE: 37

Gly Ser Lys Asp Asp Thr Leu Lys Glu Glu Pro Ser Ala Ala Pro
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic- mPD1-216 peptide

<400> SEQUENCE: 38

Lys Glu Glu Pro Ser Ala Ala Pro Val Pro Ser Val Ala Tyr Glu
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic- mPDL1-13 peptide

<400> SEQUENCE: 39

Cys His Leu Leu Arg Ala Phe Thr Ile Thr Ala Pro Lys Asp Leu
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic- mPDL1-76 peptide

<400> SEQUENCE: 40

Pro Gln His Ser Asn Phe Arg Gly Arg Ala Ser Leu Pro Lys Asp
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic- mPDL1228 peptide

<400> SEQUENCE: 41

Leu Pro Ala Thr His Pro Pro Gln Asn Arg Thr His Trp Val Leu
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic- hPD1-21 peptide

<400> SEQUENCE: 42

Gly Trp Arg Pro Gly Trp Phe Leu Asp Ser Pro Asp Arg Pro Trp
1               5                   10                  15

<210> SEQ ID NO 43
<211> LENGTH: 19
<212> TYPE: PRT
<213> ORGANISM: Artificial Sequence
<220> FEATURE:
<223> OTHER INFORMATION: Synthetic- hPD1-61 peptide

<400> SEQUENCE: 43

Glu Ser Phe Val Leu Asn Trp Tyr Arg Met Ser Pro Ser Asn Gln Thr
1               5                   10                  15

Asp Lys Leu

<210> SEQ ID NO 44
<211> LENGTH: 15
<212> TYPE: PRT
<213> ORGANISM: Artificial Sequence
<220> FEATURE:
<223> OTHER INFORMATION: Synthetic- hPD1-94 peptide

<400> SEQUENCE: 44

Gln Asp Cys Arg Phe Arg Val Thr Gln Leu Pro Asn Gly Arg Asp
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Synthetic- hPD1-117 peptide

<400> SEQUENCE: 45

Arg Arg Asn Asp Ser Gly Thr Tyr Leu Cys Gly Ala Ile Ser Leu

<210> SEQ ID NO 46
<211> LENGTH: 15
<212> TYPE: PRT
<213> ORGANISM: Artificial Sequence
<220> FEATURE:
<223> OTHER INFORMATION: Synthetic hPD1-193 peptide

<400> SEQUENCE: 46

Leu Ala Val Ile Cys Ser Arg Ala Ala Arg Gly Thr Ile Gly Ala
1               5                   10                  15

<210> SEQ ID NO 47
<211> LENGTH: 19
<212> TYPE: PRT
<213> ORGANISM: Artificial Sequence
<220> FEATURE:
<223> OTHER INFORMATION: Synthetic- hPD1-193L peptide

<400> SEQUENCE: 47

Leu Ala Val Ile Cys Ser Arg Ala Ala Arg Gly Thr Ile Gly Ala Arg
1               5                   10                  15

Arg Thr Gly

<210> SEQ ID NO 48
<211> LENGTH: 15
<212> TYPE: PRT
<213> ORGANISM: Artificial Sequence
<220> FEATURE:
<223> OTHER INFORMATION: Synthetic- hPD1-205 peptide

<400> SEQUENCE: 48

Arg Arg Thr Gly Gln Pro Leu Lys Glu Asp Pro Ser Ala Val Pro
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic- hPD1-216 peptide

<400> SEQUENCE: 49

Lys Glu Asp Pro Ser Ala Val Pro Val Phe Ser Val Asp Tyr Gly
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic- hPDL1-13 peptide

<400> SEQUENCE: 50

Trp His Leu Leu Asn Ala Phe Thr Val Thr Val Pro Lys Asp Leu
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic- hPDL1-76 peptide

<400> SEQUENCE: 51

```
Val Gln His Ser Ser Tyr Arg Gln Arg Ala Arg Leu Leu Lys Asp
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic- hPDL1-112 peptide

<400> SEQUENCE: 52

Tyr Arg Cys Met Ile Ser Tyr Gly Gly Ala Asp Tyr Lys Arg Ile
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic- hPDL1-228 peptide

<400> SEQUENCE: 53

Leu Pro Leu Ala His Pro Pro Asn Glu Arg Thr His Leu Val Ile
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic- hPDL1-255 peptide

<400> SEQUENCE: 54

Leu Thr Phe Ile Phe Arg Leu Arg Lys Gly Arg Met Met Asp Val
1               5                   10                  15
```